United States Patent
Peter et al.

(10) Patent No.: US 11,312,958 B2
(45) Date of Patent: Apr. 26, 2022

(54) COMPONENTS AND METHODS FOR PRODUCING TOXIC RNAS IN EUKARYOTIC CELLS

(71) Applicant: Northwestern University, Evanston, IL (US)

(72) Inventors: Marcus E. Peter, Chicago, IL (US); Andrea E. Murmann, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/824,589

(22) Filed: Mar. 19, 2020

(65) Prior Publication Data

US 2020/0299694 A1  Sep. 24, 2020

Related U.S. Application Data

(60) Provisional application No. 62/821,776, filed on Mar. 21, 2019.

(51) Int. Cl.
| | | |
|---|---|---|
| C07H 21/02 | (2006.01) | |
| C12N 15/113 | (2010.01) | |
| C12N 15/86 | (2006.01) | |

(52) U.S. Cl.
CPC ............ *C12N 15/113* (2013.01); *C12N 15/86* (2013.01); *C12N 2310/14* (2013.01); *C12N 2310/531* (2013.01)

(58) Field of Classification Search
CPC .......................... C12N 15/113; C12N 2310/531
See application file for complete search history.

(56) References Cited

U.S. PATENT DOCUMENTS

| | | | |
|---|---|---|---|
| 4,458,066 | A | 7/1984 | Caruthers |
| 10,934,547 | B2 | 3/2021 | Peter |
| 2018/0251762 | A1 | 9/2018 | Peter |
| 2018/0320187 | A1* | 11/2018 | Peter .................... C12N 15/113 |
| 2020/0299697 | A1 | 9/2020 | Peter |

FOREIGN PATENT DOCUMENTS

| | | |
|---|---|---|
| WO | 2018152523 A1 | 8/2018 |
| WO | 2018152524 A1 | 8/2018 |

OTHER PUBLICATIONS

Putzbach et al. (BioRxiv, 2017, pp. 1-74).*
Murmann et al. (Embo Rep, 2018, 19:e45336, 1-15).*
Hammond et al. (FEBS Letters, 579, 2005, 5822-5829).*
Wojciechowska M, et al. (2011) Cellular toxicity of expanded RNA repeats: focus on RNA foci. Hum Mol Genet 20: 3811-21.
Yang JS, et al. (2011). Alternative miRNA biogenesis pathways and the interpretation of core miRNA pathway mutants. Mol Cell. 43:892-903.
Yu Z, et al (2011) Triplet repeat-derived siRNAs enhance RNA-mediated toxicity in a *Drosophila* model for myotonic dystrophy. PLoS Genet 7: e1001340.
Zamudio Jr, et al (2014) Argonaute-bound small RNAs from promoter-proximal RNA polymerase II. Cell 156: 920-34.
Andaloussi, Sel, et al. "Exosomes for targeted siRNA delivery across biological barriers." Advanced drug delivery reviews 65.3 (2013): 391-397.
Banez-Coronel M, et al (2012) A pathogenic mechanism in Huntington's disease involves small CAG-repeated RNAs with neurotoxic activity. PLoS Genet 8: e1002481.
Beg MS, et al. Phase I study of MRX34, a liposomal miR-34a mimic, administered twice weekly in patients with advanced solid tumors. Invest New Drugs 35, 180-188 (2017).
Bilen J, et al (2006) MicroRNA pathways modulate polyglutamine-induced neurodegeneration. Mol Cell 24: 157-63.
Bogerd HP, et al. (2014). Derivation and characterization of Dicer- and microRNA-deficient human cells. RNA. 20:923-37.
Bramsen JB, et al. A large-scale chemical modification screen identifies design rules to generate siRNAs with high activity, high stability and low toxicity. Nucleic Acids Res 37, 2867-2881 (2009).
Coarelli G, et al. (2017) Low cancer prevalence in polyglutamine expansion diseases. Neurology 88: 1114-1119.
De Mezer M, et al. (2011). Mutant CAG repeats of Huntingtin transcript fold into hairpins, form nuclear foci and are targets for RNA interference. Nucleic Acids Res. 39:3852-63.
Di Martino MT, et al. Synthetic miR-34a mimics as a novel therapeutic agent for multiple myeloma: in vitro and in vivo evidence. Clin Cancer Res 18, 6260-6270 (2012).
Eulalio A, et al. (2008). GW182 interaction with Argonaute is essential for miRNA-mediated translational repression and mRNA decay. Nat Struct Mol Biol. 15:346-53.
Foulkes WD, et al. (2014). DICER1: mutations, microRNAs and mechanisms. Nat Rev Cancer. 14:662-72.
Gao QQ, et al. (2018). 6mer seed toxicity in tumor suppressive miRNAs. Nature Comm. 9:4504.
Gatchel Jr, et al. (2005) Diseases of unstable repeat expansion: mechanisms and common principles. Nat Rev Genet 6: 743-55.
Giovannucci E, et al. (1997) The CAG repeat within the androgen receptor gene and its relationship to prostate cancer. Proc Natl Acad Sci U S A 94: 3320-3.

(Continued)

*Primary Examiner* — Amy H Bowman
(74) *Attorney, Agent, or Firm* — Quarles & Brady LLP

(57) ABSTRACT

Disclosed are components and methods for producing toxic RNAs and/or extracellular vesicles comprising the toxic RNAs in cells that are resistant to the toxic RNAs, which toxic RNAs may include toxic shRNA/siRNA and/or toxic pre-miRNA/miRNA. The disclosed components may include engineered cells that can be utilized to express the toxic RNAs, in which the engineered cells do not express one or more genes that are required for processing the toxic RNAs for RNA interference (RNAi) and/or one or more genes that are required for executing RNAi. The toxic RNAs and/or extracellular vesicles comprising the toxic RNAs may be utilized in methods for treating diseases and disorders through RNAi.

7 Claims, 7 Drawing Sheets
Specification includes a Sequence Listing.

(56) References Cited

OTHER PUBLICATIONS

Hakimi JM, et al (1997) Androgen receptor variants with short glutamine or glycine repeats may identify unique subpopulations of men with prostate cancer. Clin Cancer Res 3: 1599-608.
Hauptmann J, et al. Biochemical isolation of Argonaute protein complexes by Ago-APP. Proc Natl Acad Sci U S A 112, 11841-11845 (2015).
Ho TH, et al. (2005) Colocalization of muscleblind with RNA foci is separable from mis-regulation of alternative splicing in myotonic dystrophy. J Cell Sci 118: 2923-33.
Hsu RJ, et al. (2011) Long tract of untranslated CAG repeats is deleterious in transgenic mice. PLoS One 6: e16417.
Hutvagner G, et al. (2001). A cellular function for the RNA-interference enzyme Dicer in the maturation of the let-7 small temporal RNA. Science. 293:834-8.
International Searching Authority. International Search Report and Written Opinion for application PCT/US2020/023716, dated Jul. 2, 2020.
Irvine RA, et al. (1995) The CAG and GGC microsatellites of the androgen receptor gene are in linkage disequilibrium in men with prostate cancer. Cancer Res 55: 1937-40.
Jiang F, et al. (2005) Dicer-1 and R3D1-L catalyze microRNA maturation in *Drosophila*. Genes Dev 19: 1674-9.
Kim YK, et al. (2016) Re-evaluation of the roles of DROSHA, Export in 5, and DICER in microRNA biogenesis. Proc Natl Acad Sci U S A 113: E1881-9.
Kozlowski P, et al. (2010) Trinucleotide repeats in human genome and exome. Nucleic Acids Res 38: 4027-39.
Krol J, et al. (2007) Ribonuclease dicer cleaves triplet repeat hairpins into shorter repeats that silence specific targets. Mol Cell 25: 575-86.
Kumar MS, et al. (2009). Dicer1 functions as a haploinsufficient tumor suppressor. Genes Dev. 23:2700-4.
Lam, JKW, et al. "siRNA versus miRNA as therapeutics for gene silencing." Molecular Therapy-Nucleic Acids 4 (2015): e252.
Leuschner PJ, et al. (2006). Cleavage of the siRNA passenger strand during RISC assembly in human cells. EMBC Rep. 7:314-20.
Lewis BP, et al. (2003). Prediction of mammalian microRNA targets. Cell. 115:787-98.
Moseley ML, et al. (2006) Bidirectional expression of CUG and CAG expansion transcripts and intranuclear polyglutamine inclusions in spinocerebellar ataxia type 8. Nat Genet 38: 758-69.
Murmann AE, et al. (2018). Trinucleotide repeat expansion diseases, RNAi and cancer. Trends in Cancer. 4:684-700.
Murmann AE, et al. Induction of DISE in ovarian cancer cells in vivo. Oncotarget 8, 84643-84658 (2017).
Nalavade R, et al (2013) Mechanisms of RNA-induced toxicity in CAG repeat disorders. Cell Death Dis 4: e752.
Napierala M, et al. (1997) CUG repeats present in myotonin kinase RNA form metastable "slippery" hairpins. J Biol Chem 272: 31079-85.
Park et al., 2018, Drosha knockout leads to enhancement of viral titers for vectors encoding miRNA-adapted shRNAs. Molecular Therapy-Nucleic Acids, 12, 591-599.
Patel M, et al. (2018). Identification of DISE-inducing shRNAs by monitoring cellular responses. Cell Cycle. 17: 506-14.
Peter ME. Let-7 and miR-200 microRNAs: guardians against pluripotency and cancer progression. Cell Cycle 8, 843-852 (2009).
Putzbach W, et al. (2017). Many si/shRNAs can kill cancer cells by targeting multiple survival genes through an off-target mechanism. eLife. 6: e29702.
Putzbach W, et al. (2018). CD95/Fas ligand mRNA is toxic to cells. eLife. 7:e38621.
Putzbach W, et al. (2018). DISE—A Seed Dependent RNAi Off-Target Effect that Kills Cancer Cells. Trends in Cancer. 4:10-9.
Ross CA (2002) Polyglutamine pathogenesis: emergence of unifying mechanisms for Huntington's disease and related disorders. Neuron 35: 819-22.
Rue L, et al. (2016) Targeting CAG repeat RNAs reduces Huntington's disease phenotype independently of huntingtin levels. J Clin Invest 126: 4319-4330.
Selbach M, et al. (2008). Widespread changes in protein synthesis induced by microRNAs. Nature. 455:58-63.
Sharp AH, et al. (1995) Widespread expression of Huntington's disease gene (IT15) protein product. Neuron 14: 1065-74.
Slabakova E, et al. (2017). Alternative mechanisms of miR-34a regulation in cancer. Cell Death Dis. 8:e3100.
Sorensen SA, et al (1999) Significantly lower incidence of cancer among patients with Huntington disease: An apoptotic effect of an expanded polyglutamine tract? Cancer 86: 1342-6.
Tsujimoto Y, et al (2004) In situ shortening of CAG repeat length within the androgen receptor gene in prostatic cancer and its possible precursors. Prostate 58: 283-90.
Turner MR, et al (2013) Reduced cancer incidence in Huntington's disease: record linkage study clue to an evolutionary trade-off? Clin Genet 83: 588-90.
Wang T, et al (2015) Identification and characterization of essential genes in the human genome. Science 350: 1096-101.
Wang Y, et al. (2008). Structure of the guide-strand-containing argonaute silencing complex. Nature. 456:209-13.

* cited by examiner

B

SEQ ID NO: 3

```
         A       A
        / \     / \
5' UGCUGCUGCUGCAGCAGCAGCAGCAGC  G
   ||||||||||||||||||||||||||
3' AACGACGACGACGACGACGACGACGACG  C
```

AR CAG hairpin (AR-3-21)

Figure 1 (continued)

pTIP-shCAG/CUG

A

Main Dicer cleavage site

```
       ▼                          C
5' GCAGCAGCAGCAGCAGCAG          T  C
   ||||||||||||||||||            
3' TTTTTGUCGUCGUCGUCGUC          G
                       ▲        G  A
                  Main Dicer cleavage site
```

SEQ ID NO: 4

Figure 2

COMPONENTS AND METHODS FOR PRODUCING TOXIC RNAS IN EUKARYOTIC CELLS

CROSS-REFERENCE TO RELATED APPLICATIONS

This application claims the benefit of U.S. Provisional Application No. 62/821,776, filed Mar. 21, 2019, the content of which is incorporated herein by reference in its entirety.

STATEMENT REGARDING FEDERALLY SPONSORED RESEARCH OR DEVELOPMENT

This invention was made with government support under CA197450 awarded by the National Institutes of Health. The government has certain rights in the invention.

SEQUENCE LISTING

A Sequence Listing accompanies this application and is submitted as an ASCII text file of the sequence listing named "702581_01724_ST25.txt" which is 25 KB in size and was created on Sep. 28, 2021. The sequence listing is electronically submitted via EFS-Web with the application and is incorporated herein by reference in its entirety.

BACKGROUND

The field of the invention relates to RNA interference (RNAi) and the use of RNAi active sequences for treating diseases and disorders. In particular, the field of the invention relates to the use of toxic RNAi active sequences for killing cancer cells and methods for producing toxic RNAi active sequences in cells.

Cancer therapy is only marginally effective and not curative because tumor cells will often develop resistance and metastasize. This resistance is driven by the enhanced mutagenesis rate cancer cells experience and is particularly effective in circumventing drugs designed to target a single molecule or pathway. We recently described DISE ("death induced by survival gene elimination"), a method to kill cancer cells through the RNAi pathway using either toxic si/shRNAs or artificial miRNAs that are expressed or introduced into cancer cells. DISE-based cancer therapy is attractive because cancer cells should not be able to develop resistance to DISE-based cancer therapy.

As such, natural delivery systems to introduce toxic RNAs to cancer cells are desirable. Extracellular vesicles, such as exosomes, are used to package nucleic acid and provide a vehicle for introducing the nucleic acid to a recipient cell. Typically, nucleic acid-containing exosomes are prepared first by a process that includes isolating exosomes from cells and then packaging the nucleic acid into the exosomes via subjecting the exosomes and the nucleic acid to electroporation. However, this process is inefficient and electroporation alters the physical properties of the exosomes, which may render the exosomes less efficient as vehicles for packaging nucleic acid for delivery to a recipient cell.

Here, the inventors disclose a process for expressing toxic RNAs in cells that are resistant to DISE. These cells can be used to prepare the toxic RNAs and/or naturally produced exosomes in which the toxic RNAs are packaged. The disclosed cells are resistant to DISE because the cells do not express either of Dicer and Ago2. As such, the disclosed cells cannot process shRNA to siRNA and pre-miRNA to miRNA, which is the function of Dicer, and/or the cells cannot execute RNAi and exhibit DISE, where Ago2 is required to execute RNAi. The disclosed cells are resistant to the effects of toxic RNAs accordingly. The inventors demonstrate that total RNA isolated from Dicer knock out cells that have been induced to express a highly toxic shRNA can kill wild-type cells when the wild-type cells are transfected with the isolated RNA. The disclosed cells similarly can be utilized to produce exosomes comprising highly toxic RNAs such as toxic shRNAs/siRNAs and/or toxic pre-miRNAs/miRNAs, which may be artificial or engineered.

SUMMARY

Disclosed are components and methods for producing toxic RNAs and/or extracellular vesicles comprising the toxic RNAs in cells that are resistant to the toxic RNAs, which toxic RNAs may include toxic shRNAs/siRNAs and/or toxic pre-miRNAs/miRNAs. The disclosed components may include engineered cells that can be utilized to express the toxic RNAs, in which the engineered cells do not express one or more genes that are required for processing toxic RNAs for RNAi and/or executing RNAi. The toxic RNAs and/or extracellular vesicles comprising the toxic RNAs may be utilized in methods for treating diseases and disorders through RNAi.

Figure 1:
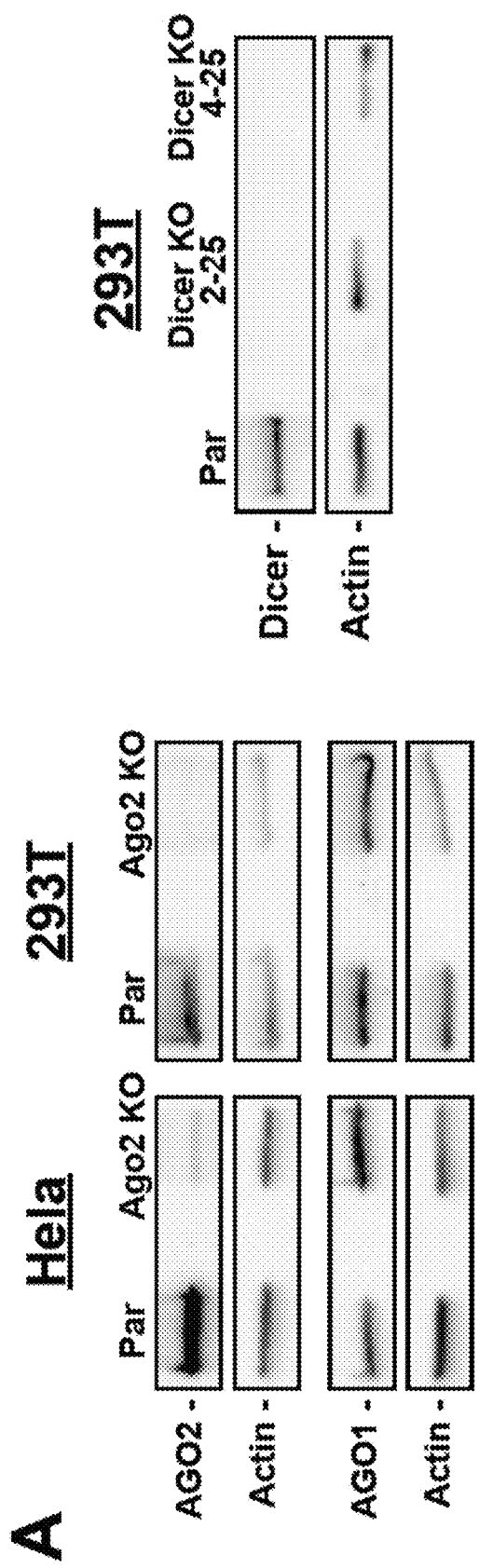
FIG. 1. Dependence of siRNA duplexes and hairpins on AGO2 and Dicer for toxicity. (A) Western blot analysis of AGO2, AGO1 and Dicer in HeLa and 293T cells deficient in expression of AGO2 or Dicer. Antibodies used: AGO1: Cell Signaling D84G10XP #5053 (1:1000); AGO2: Abcam #32381 (1:500); Dicer: Cell Signaling (D38E7) Rabbit mAb #5362 (1:1000); Actin: Santa Cruz #sc-47778 (1:10,000), all in 5% milk/TBST. (B) Structure of a AR derived CAG rich hairpin used as a toxic shRNA (SEQ ID NO: 3). (C-E) Cell confluency over time of different cells reverse transfected with the indicated si and shRNAs at 10 nM. In Figure (C) HeLa parental: top line is siNT1; middle line is si34a$^{Seed}$; bottom line is siCAG/CUG; HeLA Ago2 ko: top line is siNT1; middle line is siCAG/CUG; bottom line is si34a$^{Seed}$. In Figure (D) 293 parental: top line is siNT1; middle line is siL3; bottom line is si34a$^{Seed}$; 293 Dicer ko (4-25): top line is siNT1; middle line is siL3; bottom line is si34a$^{Seed}$. In Figure (E) 294T parental: top line is siNT1; middle line at 100 hours is AR CAG HP; bottom line at 100 hour is sh-siL3; 293Ago2ko: top line is siNT1; middle line is AR CAG HP; bottom line is sh-siL3; 293Dicer ko (4-25): top line is siNT1; middle line is AR CAG HP; bottom line is sh-siL3.
Figure 1:
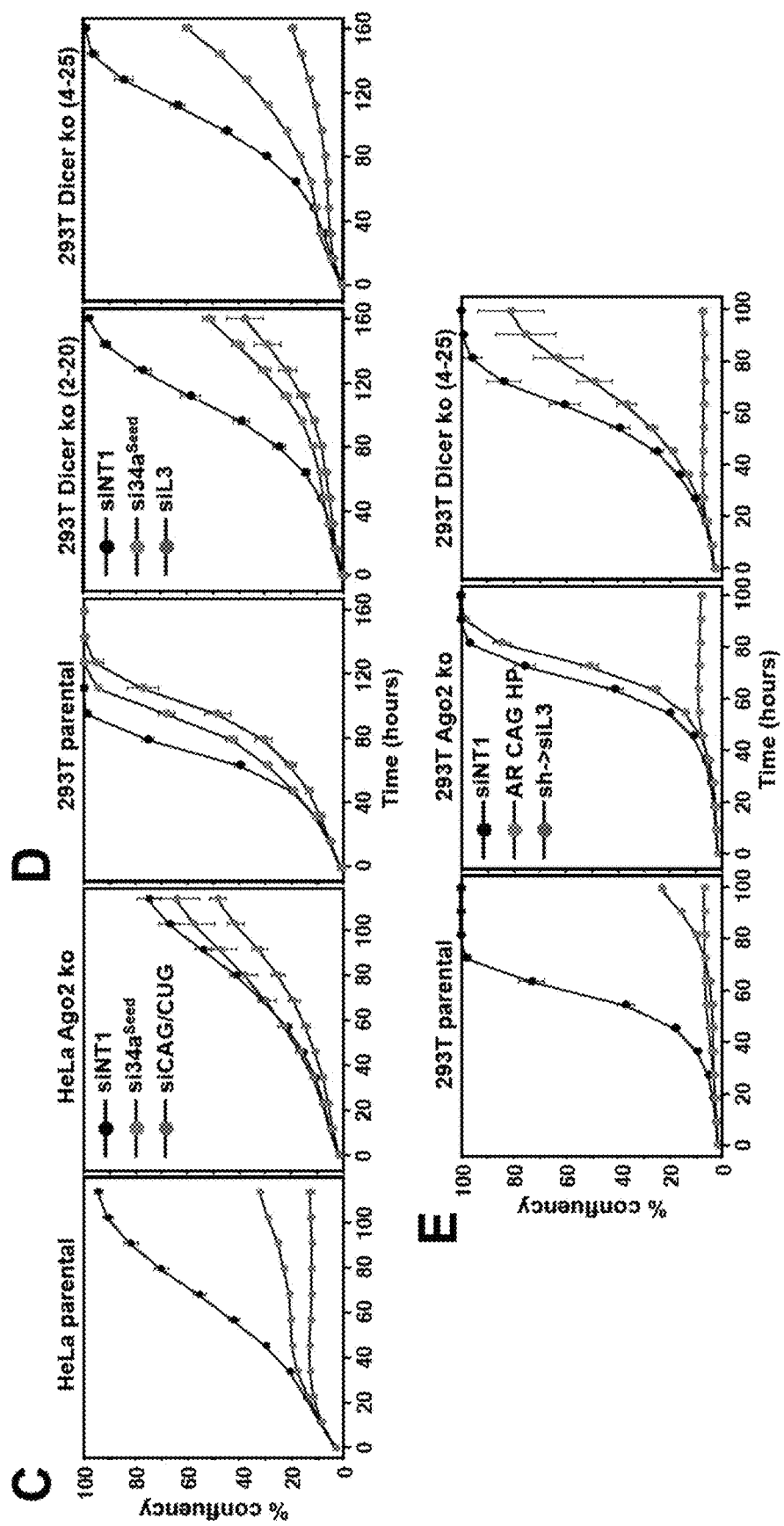

Cell confluency over time of HeyA8 cells transfected with the indicated amount of total small RNA extracted from either pTIP-Shr or pTIP-shCAG/CUG expressing Dicer k.o. 293T cells after treatment with 0.1 mg/ml DOX for 48 hrs.

DETAILED DESCRIPTION

The present invention is described herein using several definitions, as set forth below and throughout the application.

Unless defined otherwise, all technical and scientific terms used herein have the same meaning as commonly understood by one of skill in the art to which the invention pertains. All definitions, as defined and used herein, should be understood to control over dictionary definitions, definitions in documents incorporated by reference, and/or ordinary meanings of the defined terms.

Unless otherwise specified or indicated by context, the terms "a", "an", and "the" should be interpreted to mean "one or more." For example, "an shRNA" or "an miRNA" should be interpreted to mean "one or more shRNA's" and "one or more miRNAs," respectively As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" should be interpreted to mean plus or minus ≤10% of the particular term and "substantially" and "significantly" should be interpreted to mean plus or minus >10% of the particular term.

As used herein, the terms "include" and "including" should be interpreted to have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

A range includes each individual member. Thus, for example, a group having 1-3 members refers to groups having 1, 2, or 3 members.

It should also be understood that, unless clearly indicated to the contrary, in any methods claimed herein that include more than one step or act, the order of the steps or acts of the method is not necessarily limited to the order in which the steps or acts of the method are recited.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, a "subject" may be interchangeable with "patient" or "individual" and means an animal, which may be a human or non-human animal, in need of treatment.

A "subject in need of treatment" may include a subject having a disease, disorder, or condition that can be treated by administering to the subject one or more therapeutic RNAs as disclosed herein. A subject in need thereof may include a subject having or at risk for developing a cell proliferative disease or disorder such as cancer. A subject in need thereof may include, but is not limited to, a subject having or at risk for developing any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus). As such, methods of treating cancers are contemplated herein, including methods of treating cancers selected from, but not limited to any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus).

As used herein, a "toxic RNA" refers to an RNA molecule that induces cell death via RNA interference (RNAi) when the RNA molecule is expressed in a cell. Toxic RNAs may include, but are not limited to toxic shRNA, toxic siRNA (which may have been processed via Dicer from a corresponding shRNA), toxic pre-miRNA which may be artificial or engineered pre-miRNA, and/or toxic miRNA (which may have been processed via Dicer from a corresponding pre-miRNA). Toxic RNAs have been disclosed in the art. (See U.S. Published Application Nos. 20180251762 and 20180320187, the contents of which are incorporated herein by reference in their entireties).

As used herein, the terms "silencing" and "inhibiting the expression of" refer to at least partial suppression of the expression of a target gene, for example, as manifested by a reduction of mRNA associated with the target gene.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

As used herein, the term "pharmaceutical composition" may be defined as a composition that includes a pharmacologically effective amount of a toxic RNA and/or extracellular particles comprising the toxic RNA and a pharmaceutically acceptable carrier for delivering the toxic RNA to target cells or target tissue. As used herein, the term "pharmaceutically acceptable carrier" refers to a carrier for administration of a therapeutic agent which facilitates the delivery of the therapeutic agent (e.g., a toxic RNA and/or extracellular particles comprising the toxic RNA) to target cells or target tissue. As used herein, the term "therapeutically effective amount" refers to that amount of a therapeutic agent that provides a therapeutic benefit in the treatment, prevention, or management of a disease or disorder (e.g., a cell proliferation disease or disorder such as cancer).

In one aspect, the present inventors have disclosed toxic RNAs that silences expression of one or more mRNA's of essential genes that are required for survival and growth of cells such as cancer cells. Preferably, the disclosed toxic RNA molecules silence the expression of multiple mRNA's of essential genes that are required for survival and growth of cells such as cancer cells through a process similar to the process called "death-induced by survival gene elimination" or "DISE."

The mechanism of action of RNA interference (RNAi) is understood by the skilled person. Interfering RNA (RNAi) generally refers to process that utilizes a single-stranded RNA (ssRNA) or double-stranded RNA (dsRNA) to inhibit expression of a target. The dsRNA is capable of targeting specific messenger RNA (mRNA) and silencing (i.e., inhibiting) the expression of a target gene. During this process, dsRNA (which may include shRNA or pre-miRNA) is enzymatically processed into short-interfering RNA (siRNA) duplexes or miRNA duplexes by a nuclease called Dicer. The anti-sense strand of the siRNA duplex or miRNA duplex is then incorporated into a cytoplasmic complex of proteins (RNA-induced silencing complex or RISC). The RISC complex containing the anti-sense siRNA strand or miRNA strand also binds mRNA which has a sequence complementary to the anti-sense strand-allowing complementary base-pairing between the anti-sense strand and the sense mRNA molecule. The mRNA molecule is then specifically cleaved by an enzyme (RNase) associated with RISC called Argonaut 2 (Ago2) resulting in specific gene silencing. For gene silencing or knock down (i.e., mRNA cleavage) to occur, anti-sense RNA has to become incorporated into the RISC. This represents an efficient process that occurs in nucleated cells during regulation of gene expression.

In particular, siRNA-mediated RNA interference may be considered to involve two-steps: (i) an initiation step, and (ii) an effector step. In the first step, input siRNA is processed into small fragments by Dicer. These small fragments are ~21-23-nucleotide in length and are called "guide RNAs." The guide RNAs can be incorporated into the protein-RNA RISC complex which is capable of degrading mRNA. As such, the RISC complex acts in the second effector step to destroy mRNAs that are recognized by the guide RNAs through base-pairing interactions via Ago2. RNA interference may be considered to involve the introduction by any means of double stranded RNA into a cell which triggers events that cause the degradation of a target RNA, and as such may be considered to be a form of post-transcriptional gene silencing. The skilled person understands how to prepare and utilize RNA molecules in RNAi. (See, e.g., Hammond et al., Nature Rev Gen 2: 110-119 (2001); and Sharp, Genes Dev 15: 485-490 (2001), the contents of which are incorporate herein by reference in their entireties).

Polynucleotides

The disclosed technology relates to nucleic acid and the use of nucleic acid for treated diseases and disorders. The terms "nucleic acid" and "oligonucleotide," as used herein, refer to polydeoxyribonucleotides (containing 2-deoxy-ribose), polyribonucleotides (containing ribose), and to any other type of polynucleotide that is an N glycoside of a purine or pyrimidine base. As used herein, the terms "A," "T," "C", "G" and "U" refer to adenine, thymine, cytosine, guanine, uracil as a nucleotide base, respectively. There is no intended distinction in length between the terms "nucleic acid," "oligonucleotide," and "polynucleotide," and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

The disclosed polynucleotides may include a fragment of a reference polynucleotide. As used herein, a "fragment" of a polynucleotide is a portion of a polynucleotide sequence which is identical in sequence to but shorter in length than a reference sequence. A fragment may comprise up to the entire length of the reference sequence, minus at least one nucleotide. For example, a fragment may comprise from 5 to 1000 contiguous nucleotides of a reference polynucleotide. In some embodiments, a fragment may comprise at least 5, 10, 15, 20, 25, 30, 40, 50, 60, 70, 80, 90, 100, 150, 250, or 500 contiguous nucleotides of a reference polynucleotide; in other embodiments a fragment may comprise no more than 5, 10, 15, 20, 25, 30, 40, 50, 60, 70, 80, 90, 100, 150, 250, or 500 contiguous nucleotides of a reference polynucleotide; in further embodiments a fragment may comprise a range of contiguous nucleotides of a reference polynucleotide bounded by any of the foregoing values (e.g. a fragment comprising 20-50 contiguous nucleotides of a reference polynucleotide). Fragments may be preferentially selected from certain regions of a molecule. The term "at least a fragment" encompasses the full length polynucleotide. A "variant," "mutant," or "derivative" of a reference polynucleotide sequence may include a fragment of the reference polynucleotide sequence.

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "promoter" as used herein refers to a cis-acting DNA sequence that directs RNA polymerase and other trans-acting transcription factors to initiate RNA transcription from the DNA template that includes the cis-acting DNA sequence. Promoters may include inducible promoter, which are promoters that can be induced to function in the presence of an effector molecule as known in the art.

As used herein, the term "complementary" in reference to a first polynucleotide sequence and a second polynucleotide sequence means that the first polynucleotide sequence will base-pair exactly with the second polynucleotide sequence throughout a stretch of nucleotides without mismatch. The term "cognate" may in reference to a first polynucleotide sequence and a second polynucleotide sequence means that the first polynucleotide sequence will base-pair with the second polynucleotide sequence throughout a stretch of nucleotides but may include one or more mismatches within the stretch of nucleotides. As used herein, the term "complementary" may refer to the ability of a first polynucleotide to hybridize with a second polynucleotide due to base-pair interactions between the nucleotide pairs of the first polynucleotide and the second polynucleotide (e.g., A:T, A:U, C:G, G:C, G:U, T:A, U:A, and U:G).

As used herein, the term "complementarity" may refer to a sequence region on an anti-sense strand that is substantially complementary to a target sequence but not fully complementary to a target sequence. Where the anti-sense strand is not fully complementary to the target sequence, mismatches may be optionally present in the terminal regions of the anti-sense strand or elsewhere in the anti-sense strand. If mismatches are present, optionally the mismatches may be present in terminal region or regions of the anti-sense strand (e.g., within 6, 5, 4, 3, or 2 nucleotides of the 5' and/or 3' terminus of the anti-sense strand).

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions." Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, Biochemistry, 47: 5336-5353, which are incorporated herein by reference).

As used herein, the term "double-stranded RNA" ("dsRNA") refers to a complex of ribonucleic acid molecules having a duplex structure comprising two anti-parallel and substantially complementary nucleic acid strands.

As used herein, the term "nucleotide overhang" refers to an unpaired nucleotide or nucleotides that extend from the 5'-end or 3'-end of a duplex structure of a dsRNA when a 5'-end of one strand of the dsRNA extends beyond the 3'-end of the other strand, or when a 3'-end of one strand of the dsRNA extends beyond the 5'-end of the other strand.

As used herein, the term "blunt" refers to a dsRNA in which there are no unpaired nucleotides at the 5'-end and/or the 3'-end of the dsRNA (i.e., no nucleotide overhang at the 5'-end or the 3'-end). A "blunt ended" dsRNA is a dsRNA that has no nucleotide overhang at the 5'-end or the 3'-end of the dsRNA molecule.

As used herein, the term "anti-sense strand" refers to a strand of a dsRNA which includes a region that is substantially complementary to a target sequence (i.e., where the target sequence has a sequence corresponding to the sense strand).

As used herein, the term "sense strand," refers to the strand of a dsRNA that includes a region that is substantially complementary to a region of the anti-sense strand and that includes a region that substantially corresponds to a region of the target sequence.

As used herein, RNAi active sequences may include "siRNA" and "shRNA" and dsRNA that is processed to provide siRNA and/or shRNA. The term "siRNA" refers to a "small interfering RNA" and the term "shRNA" refers to "short hairpin RNA." RNA interference (RNAi) refers to the process of sequence-specific post-transcriptional gene silencing in a cell or an animal mediated by siRNA and/or shRNA.

As used herein, the term "siRNA targeted against mRNA" refers to siRNA specifically promote degradation of the targeted mRNA via sequence-specific complementary multiple base pairings (e.g., at least 6 contiguous base-pairs between the siRNA and the target mRNA at optionally at least 7, 8, 9, 10, 11, 12, 13, 14, 15, 16, 17, 18, 19, 20, 21, 22, or 23 contiguous base-pairs between the siRNA and the target mRNA).

As used herein, RNAi active sequences may include "pre-miRNA" and "miRNA" and dsRNA that is processed to provide pre-miRNA and miRNA. The term "pre-miRNA" refers to a "pre-micro RNA" and the term "miRNA" refers to "micro RNA." RNA interference (RNAi) refers to the process of sequence-specific post-transcriptional gene silencing in a cell or an animal mediated by pre-miRNA and/or miRNA.

The terms "target, "target sequence", "target region", and "target nucleic acid," as used herein, are synonymous and refer to a region or sequence of a nucleic acid which may be selected as an anti-sense sequence of a strand of siRNA or shRNA and/or pre-miRNA or miRNA (e.g., a passenger strand and/or a guide strand) which is substantially complementary to and hybridizes to the target sequence as discussed herein. A target sequence may refer to a contiguous portion of a nucleotide sequence of an mRNA molecule of a particular gene, including but not limited to, genes that are essential for survival and/or growth of cells and in particular cancer cells. For example, a target sequence of an shRNA refers to a mRNA sequence of a gene that is targeted by the shRNA due to complementarity between a strand of the shRNA and the mRNA sequence and to which the strand of the shRNA hybridizes when brought into contact with the mRNA sequence.

As used herein, the term "transfecting" means "introducing into a cell" a molecule, which may include a polynucleotide molecule such as dsRNA or a vector that expresses an RNA molecule (e.g., a shRNA or a pre-miRNA). "Transfecting" means facilitating uptake or absorption into the cell, as is understood by the skilled person. Absorption or uptake can occur or may be facilitated through passive diffusive or active cellular processes, or through the use of auxiliary agents or devices. Transfection into a cell includes methods known in the art such as electroporation and lipofection.

For purposes of this application, the anti-sense strand of the disclosed RNA molecules may comprise a contiguous nucleotide sequence, where the base sequence of the anti-sense strand has substantial or complete sequence complementarity to the base sequence of a contiguous nucleotide sequence of corresponding length contained in an mRNA sequence of the targeted mRNA (e.g., in a non-coding 3'-end of an mRNA sequence). Substantial complementary permits some nucleotide mismatches (i.e., non-pairing nucleotides) and as such, the anti-sense strand of the siRNA need not have full complementarity.

In some embodiments, at least a portion of an anti-sense strand of the disclosed RNA molecules comprises or consists of a sequence that is 100% complementary to a target sequence or a portion thereof. In another embodiment, at least a portion of an anti-sense strand of an siRNA molecule comprises or consists of a sequence that is at least about 90%, 95%, or 99% complementary to a target sequence or a portion thereof. For purposes of this application, the anti-sense strand of the disclosed RNA molecules preferably comprises or consists of a sequence that specifically hybridizes to a target sequence or a portion thereof so as to inhibit expression of the target mRNA.

In some embodiments, the disclosed RNAs may include repeat sequences. For example, in some embodiments, the disclosed RNAs may include trinucleotide repeats such as any of: $(AAA)_n$, $(AAC)_n$, $(AAG)_n$, $(AAU)_n$, $(ACA)_n$, $(ACC)_n$, $(ACG)_n$, $(ACU)_n$, $(AGA)_n$, $(AGC)_n$, $(AGG)_n$, $(AGU)_n$, $(AUA)_n$, $(AUC)_n$, $(AUG)_n$, $(AUU)_n$, $(CAA)_n$, $(CAC)_n$, $(CAG)_n$, $(CAU)_n$, $(CCA)_n$, $(CCC)_n$, $(CCG)_n$, $(CCU)_n$, $(CGA)_n$, $(CGC)_n$, $(CGG)_n$, $(CGU)_n$, $(CUA)_n$, $(CUC)_n$, $(CUG)_n$, $(CUU)_n$, $(GAA)_n$, $(GAC)_n$, $(GAG)_n$, $(GAU)_n$, $(GCA)_n$, $(GCC)_n$, $(GCG)_n$, $(GCU)_n$, $(GGA)_n$, $(GGC)_n$, $(GGG)_n$, $(GGU)_n$, $(GUA)_n$, $(GUC)_n$, $(GUG)_n$, $(GUU)_n$, $(UAA)_n$, $(UAC)_n$, $(UAG)_n$, $(UAU)_n$, $(UCA)_n$, $(UCC)_n$, $(UCG)_n$, $(UCU)_n$, $(UGA)_n$, $(UGC)_n$, $(UGG)_n$, $(UGU)_n$, $(UUA)_n$, $(UUC)_n$, $(UUG)_n$, and $(UUU)_n$, where n is an integer, typically selected from 3, 4, 5, 6, 7, 8, 9, 10, 11, 12, 13, 14, 15, to about 100 or higher. Preferably, the disclosed RNAs may include trinucleotide repeats such as any of: $(AGC)_n$, $(CAG)_n$, $(CUG)_n$, $(GCA)_n$, $(GGU)_n$, and $(UGC)_n$, where n is an integer, typically selected from 3, 4, 5, 6, 7, 8, 9, 10, 11, 12, 13, 14, 15, to about 100 or higher.

Methods for preparing and isolating RNA also are known in the art. (See, e.g., Sambrook et al., Molecular Cloning, A Laboratory Manual (2.sup.nd Ed., 1989), the content of which is incorporated herein by reference in its entirety). The disclosed RNA may be prepared and isolated from cells as disclosed herein, such as eukaryotic cells.

In one embodiment, the disclosed RNAs comprise a double stranded region of about 15 to about 30 nucleotides in length. Preferably, the disclosed RNAs are about 20-25 nucleotides in length. The disclosed RNAs of the present invention are capable of silencing the expression of a target sequence in vitro and in vivo.

In one embodiment, the RNA disclosed herein comprises a hairpin loop structure and may be referred to as shRNA which may be processed to a siRNA. In other embodiments, the RNA disclosed herein may be referred to as pre-miRNA, which is either naturally occurring or artificial or engineered, and may be processed to a miRNA, which in turn is either naturally occurring or artificial or engineered In some embodiments, the disclosed RNA molecules are capable of silencing one or more target mRNAs and may reduce expression of the one or more target mRNAs by at least about 20%, 30%, 40%, 50%, 60%, 70%, 80%, 90%, or 100% relative to a control RNA molecule (e.g., a molecule not exhibiting substantial complementarity with the target mRNA). As such, in some embodiments, the presently disclosed RNA molecules targeting the mRNA of essential genes may be used to down-regulate or inhibit the expression of essential genes (e.g., by at least about 20%, 30%, 40%, 50%, 60%, 70%, 80%, 90%, or 100% relative to a control RNA molecule).

The disclosed RNA molecules may conveniently be delivered to a target cell or a target tissue through a number of delivery systems. For example, RNA may be delivered via electroporation, lipofection, calcium phosphate precipitation, plasmids, viral vectors that express the RNA, viral nucleic acids, phage nucleic acids, phages, cosmids, nanoparticles or via transfer of genetic material in cells or carriers such as cationic liposomes or extracellular particles that comprise the disclosed RNA molecules. In one embodiment, transfection of RNA may employ viral vectors, chemical transfectants, or physico-mechanical methods such as electroporation and direct diffusion of DNA.

Components and Methods for Producing Toxic RNAs in Eukaryotic Cells

The disclosed subject matter relates to components and methods for producing toxic RNAs in eukaryotic cells. The disclosed components and methods may be utilized for producing toxic shRNAs/siRNAs and/or pre-miRNAs/miRNAs and/or extracellular vesicles comprising the toxic shRNAs/siRNAs and/or toxic pre-miRNAs/miRNAs in cells that are resistant to the toxic shRNAs/siRNAs and the toxic pre-miRNAs/miRNAs. The disclosed components may include engineered cells that can be utilized to express the toxic shRNAs/siRNAs and/or the toxic pre-miRNAs/miRNAs, in which the engineered cells do not express one or more genes that are required for processing shRNAs and/or pre-miRNAs to siRNAs and miRNAs, respectively, and/or executing RNAi. The toxic shRNAs/siRNAs and/or pre-miRNAs/miRNAs and/or extracellular vesicles comprising the toxic shRNAs/siRNAs and/or the toxic pre-miRNAs/miRNAs that are produced by the disclosed methods may be utilized in methods for treating diseases and disorders through RNAi.

In some embodiments, the disclosed methods for producing toxic shRNA/siRNA or toxic pre-miRNA/miRNA, or extracellular particles comprising the toxic shRNA/siRNA or the toxic pre-miRNA/miRNA, the methods comprise expressing the toxic shRNA/siRNA or the toxic pre-miRNA/miRNA in a eukaryotic cell that is deficient in a gene that is required for processing of shRNA to siRNA or pre-miRNA to miRNA, and/or that is deficient in a gene that is required for executing RNA interference (RNAi).

In some embodiments of the disclosed methods, the eukaryotic cell is deficient in Dicer. For example, the eukaryotic cell may be engineered to be deficient in the Dicer gene (e.g., a least a portion of the Dicer gene may be deleted optionally via CRISPR technology) and/or the eukaryotic cell may be engineered to not express the Dicer protein. The human Dicer1 gene entry is provided at the website for the National Center for Biotechnology Information under Gene ID: 23405, updated on 12 Mar. 2019, the content of which is incorporated herein by reference in its entirety. The Dicer gene encodes a protein having the amino acid sequence of SEQ ID NO:1. As such, in some embodiments, the eukaryotic cell may be engineered to be deficient in a gene that encodes the protein of SEQ ID NO:1 or a fragment thereof, and/or the eukaryotic cell may be engineered to not express a protein expressing SEQ ID NO:1 or a fragment thereof.

In some embodiments of the disclosed methods, the eukaryotic cell is deficient in AGO2. For example, the eukaryotic cell may be engineered to be deficient in the AGO2 gene (e.g., a least a portion of the AGO2 gene may be deleted optionally via CRISPR technology) and/or the eukaryotic cell may be engineered to not express the AGO2 protein. The human AGO2 gene entry is provided at the website for the National Center for Biotechnology Information under Gene ID: 27161, updated on 5 Mar. 2019, the content of which is incorporated herein by reference in its entirety. The AGO2 gene encodes a protein having the amino acid sequence of SEQ ID NO:2. As such, in some embodiments, the eukaryotic cell may be engineered to be deficient in a gene that encodes the protein of SEQ ID NO:2 or a fragment thereof, and/or the eukaryotic cell may be engineered to not express a protein expressing SEQ ID NO:2 or a fragment thereof.

The disclosed methods may be performed in order to produce toxic RNA, such as toxic shRNA/siRNA and/or toxic pre-miRNA/miRNA. In other embodiments, the disclosed methods may be performed in order to produce extracellular particles comprising toxic RNA, for example, extracellular particles comprising toxic shRNA/siRNA and/or toxic pre-miRNA/miRNA. The extracellular particles may include exosomes that are released from the engineered eukaryotic cells disclosed herein.

In the disclosed methods, a toxic RNA is expressed in an engineered cell as disclosed herein. In some embodiments, the toxic RNA is expressed via transfecting or infecting the engineered cell with a vector that expresses the toxic RNA. In some embodiments, the vector comprises an inducible promoter for expressing the toxic RNA. Suitable vectors may include, but are not limited to, viral vectors such as adenovirus-associated viral (AAV) vectors and lentiviral vectors.

In the disclosed methods, a toxic RNA is expressed in an engineered cell as disclosed herein. In some embodiments, the toxic RNA is a toxic shRNA or toxic siRNA (i.e., a toxic shRNA/siRNA) which comprises a first strand that substantially hybridizes to a second strand. In some embodiments, the first strand and the second strand may be referred to as a passenger strand and a guide strand, respectively. In some embodiments, the toxic shRNA/siRNA comprises a passenger strand, a guide strand, and a trinucleotide repeat sequence $(X_1X_2X_3)_n$ present in the passenger strand, the guide strand, or both strands, where $X_1$, $X_2$, and $X_3$ independently are selected from any ribonucleotide A, C, G, and U, and n is an integer from 3-10. Preferably, the trinucleotide repeat sequence has a GC content of at least 33% or a GC content of at least 66%. Suitable trinucleotide repeat sequences may include, but are not limited to a trinucleotide repeat sequence selected from the group consisting of $(ACC)_n$, $(ACG)_n$, $(AGC)_n$, $(AGG)_n$, $(CAC)_n$, $(CAG)_n$, $(CCA)_n$, $(CCC)_n$, $(CCG)_n$, $(CCU)_n$, $(CGA)_n$, $(CGC)_n$, $(CGG)_n$, $(CGU)_n$, $(CUC)_n$, $(CUG)_n$, $(GAC)_n$, $(GAG)_n$, $(GCA)_n$, $(GCC)_n$, $(GCG)_n$, $(GCU)_n$, $(GGA)_n$, $(GGC)_n$, $(GGG)_n$, $(GGU)_n$, $(GUC)_n$, $(GUG)_n$, $(UCC)_n$, $(UCG)_n$, $(UGC)_n$, and $(UGG)_n$, where N is an integer from 3-10. In some embodiments, the trinucleotide repeat sequence is CAG or CUG and the trinucleotide repeat sequence is present in the guide strand.

In some embodiments, the toxic RNA is a toxic shRNA or toxic siRNA (i.e., a toxic shRNA/siRNA), where the shRNA/siRNA comprises a dsRNA sequence defined as follows:

```
5'- P01 P02 P03 P04 P05 P06 P07 P08 P09 P10 P11 P12 P13 P14 P15 P16 P17 P18 P19
    *   *   *   *   *   *   *   *   *   *   *   *   |   |   |   |   |   |   *
3'- G19 G18 G17 G16 G15 G14 G13 G12 G11 G10 G09 G08 G07 G06 G05 G04 G03 G02 G01
``` where:

G01 through G19 and P01 through P19 are any ribonucleotide selected from A, U, G, and C, provided that:

G01 is A or U;

G02, G03, G04, G05, G06, and G07 are complementary to P18, P17, P16, P15, P14, and P13, respectively;

the percentage GC content of the region from G02 to G07 is 70-100%;

the percentage GC content of the region from G08 to G16 is 0-30%; and the percentage GC content of the region from G17 to G19 is 31-100%.

Optionally, the dsRNA may be defined as follows:

```
5'-P01 P02 P03 P04 P05 P06 P07 P08 P09 P10 P11 P12 P13 P14 P15 P16 P17 P18 P19 P20 P21-3'
   *   *   *   *   *   *   *   *   *   *   *   *   |   |   |   |   |   |   *
3'-G21 G20 G19 G18 G17 G16 G15 G14 G13 G12 G11 G10 G09 G08 G07 G06 G05 G04 G03 G02 G01-5'
``` wherein:

G20, G21, P20, and P21 are any nucleotide.

Optionally, G02, G03, G04, G05, G06, and G07 may comprise the sequence GGNNNN where N is any nucleotide. Preferably, G02, G03, G04, G05, G06, and G07 have a GC content of greater than about 80%. Preferably, G02, G03, G04, G05, G06, and G07 comprise the sequence NNNNNN, which is a polynucleotide sequence present in the 3' UTR of an mRNA for a tumor suppressor gene. Preferably, the contiguous sequence of G02 through G07 is selected from the group consisting of GGGCAG, GGGGCU, GGGCUG, GGGCGA, GGGGGC, GGGGGU, GGGCGG, GGGUGG, GGUGGG, GGCUGG, GGGGCA, GGGGUC, GGCAGC, GAAGAU, GGUGGU, GGUGGA, GGGCAA, GGGCAU, GGAGGU, GGGGCC, GGGGCG, GUCUUC, GGAGCU, GGGAGA, GGGCGU, GGCGGU, GCAGGG, GGGAGU, CGGGGC, CUGGGC, GCAGGC, GGGCGC, GCUAAC, GGCGGG, GGGUGU, GGGUGC, GGGGGA, GAGGGU, GCGGGC, GUGGGC, GGGGUG, GGGAUC, GUAGUC, GACAGC, GCCUGU, GGUGCU, GGAGGA, GGGCCU, GCGGGG, GAGGGC, GGAUGC, GGGUGA, GCGGGU, UCUGGG, AGCUGG, GUGGGG, GGGCCG, GGAGGC, GGCUAU, CGUUGC, AGGGCC, GUUGCC, GAUGCU, GAGGGG, GUAGGC, GCUGGG, GUCUCC, AGUGGG, GGCUCU, GAAGUC, GUGGGU, GGCAGG, GGUGGC, GGCUAC, GCUAAU, GAUACC, GAUGCC, CCUGGG, GGGAGC, GAUGGC, CGGGUC, CGGGGG, UGGGGG, GUAGGU, GGGUAG, AGCGGC, GCGGCG, CGGGCC, CGCGGC, GUUUCC, GGCAUU, GGGGGG, GCUAGC, GCAGGU, GGGGAU, GGUGCC, GGCGGA, AGGCUC, ACAGAU, CCAUGG, AGUUGC, GGCUGC, ACUGGG, UGGCGG, GCGGUU, GGCGGC, GACAUC, GGGCUA, UGUAGU, GGAGCC, CCGACC, GGGCCA, GGGCUC, GGCGAU, AGGGGG, GGCCGG, AACAUC, GUCUGC, UGCCUG, GUCUCU, GUCCUC, CGUUCC, CUGGGA, GCGUGC, CGGGCU, GGCAGU, CGGGGU, GGUAGG, ACACCU, GUCAUC, GCCGGC, AGGGGC, GGCCUC, GGAGGG, GGUGUU, GGCAUG, UAUCCC, CGCCGC, AGGUGC, GACUGC, GCCUUC, AGGAGG, CGGAGG, GUCUGG, AGCUGC, GGCAUC, GCUGCU, CGGUGG, GUGUUC, GUCCAC, GGGCUU, GGCCGC, GGGUCU, GGCCGU, GGUAGU, ACAUCU, GCCGGU, AGCGGU, GGUUGG, AGGGUC, GGCUAG, AACCCC, GGUGAC, GUUGGG, GUAUCC, GGGGUU, GCUAUC, GGGGAG, CGGCGG, GAACUC, ACGGGC, GUAGGG, GGGUCC, CAGGCC, GGGAGG, GUUCAC, GGUGCG, ACAGGC, AGCGGG, ACAUGC, CAUGCU, CUUGGC, GUAGCU, CCGGGC, CGUAGC, GAAGCC, ACUUGG, GGCUCC, UGUAUC, GGCUUC, ACGACC, UCGGGC, GCCGAC, GGCUCA, GGCGAC, ACAGAC, CGGCUC, UCGUGC, GUUCCU, and GUCUGU.

In some embodiments, the toxic shRNA/siRNA is an shRNA illustrated as follows:

```
5'- P01 P02 P03 P04 P05 P06 P07 P08 P09 P10 P11 P12 P13 P14 P15 P16 P17 P18 P19-Lo
     *   *   *   *   *   *   *   *   *   *   *   *   |   |   |   |   |   *   )
3'- G19 G18 G17 G16 G15 G14 G13 G12 G11 G10 G09 G08 G07 G06 G05 G04 G03 G02 G01-po
``` where:

Lo
)
po comprises a polynucleotide loop sequence.

Also disclosed herein, are extracellular particles prepared by any of the disclosed methods. For example, the methods may be performed by expressing toxic RNA as disclosed herein in an engineered cell as disclosed herein and extracellular particles comprising the toxic RNA may be isolated from media in which the engineered cell has been grown. Extracellular particles may include exosomes.

Also disclosed herein are pharmaceutical compositions. The disclosed pharmaceutical compositions may comprise extracellular particles as disclosed herein and optionally may comprise a pharmaceutical carrier, diluent, or excipient. In some embodiments, the disclosed pharmaceutical compositions comprise therapeutic RNA and/or comprising extracellular particles comprising therapeutic RNA. In some embodiments, the pharmaceutical compositions optionally may comprise one or more therapeutic agents for inhibiting the gene activity of one or more essential genes and a pharmaceutical acceptable carrier. Pharmaceutically acceptable carriers include, but are not limited to, excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Pharmaceutical compositions containing RNA may be administered to a mammal in vivo to treat cancer.

Also disclosed herein are methods of treating a disease or disorder in a subject in need thereof, the method comprising administering to the subject pharmaceutical compositions as disclosed herein. Optionally, the disease or disorder is a cell proliferative disease or disorder such as cancer.

ILLUSTRATIVE EMBODIMENTS

The embodiments described below are illustrative of the methods, compositions, and systems disclosed herein and are not intended to be limiting.

1. A first illustrative embodiment includes method for producing toxic RNA or extracellular particles comprising the toxic RNA, the method comprising expressing the toxic RNA in a eukaryotic cell that is deficient in a gene that is required for processing the toxic RNA for RNA interference (RNAi) and/or that is deficient in a gene that is required for executing RNAi.

2. The method of embodiment 1, wherein the toxic RNA is toxic shRNA, toxic siRNA, toxic pre-miRNA, or toxic miRNA, which may be artificial or engineered.

3. The method embodiment 1 or 2, wherein the wherein the eukaryotic cell is deficient in Dicer.

4. The method of embodiment 3, wherein the eukaryotic cell has been engineered to be deficient in the Dicer gene (e.g., via CRISPR technology) and/or the eukaryotic cell has been engineered to not express the Dicer protein.

5. The method of any of the foregoing embodiments, wherein the eukaryotic cell is deficient in AGO2.

6. The method of embodiment 5, wherein the eukaryotic cell has been engineered to be deficient in the AGO2 gene (e.g., via CRISPR technology) and/or the eukaryotic cell has been engineered to not express the AGO2 protein.

7. The method of any of the foregoing embodiments, wherein the method is for producing extracellular particles comprising the toxic RNA and the method further comprises isolating the extracellular particles comprising the toxic RNA from the eukaryotic cell, optionally wherein the extracellular particles comprise exosomes.

8. The method of any of the foregoing embodiments, wherein the method comprises expressing a toxic shRNA or a toxic pre-miRNA in the cell via transfecting or infecting the cell with a vector that expresses the toxic shRNA or the toxic pre-miRNA.

9. The method of embodiment 8, wherein the vector comprises an inducible promoter for expressing the toxic shRNA or the toxic pre-miRNA.

10. The method of embodiment 8 or 9, wherein the vector is a viral vector.

11. The method of any of the foregoing embodiments, wherein the toxic RNA is a toxic shRNA/siRNA comprising a passenger strand, a guide strand, and a trinucleotide repeat sequence $(X_1X_2X_3)_n$ present in the passenger strand, the guide strand, or both strands, wherein $X_1$, $X_2$, and $X_3$ independently are selected from any ribonucleotide A, C, G, and U, and n is an integer from 3-10.

12. The method of embodiment 11, wherein the trinucleotide repeat sequence has a GC content of at least 33%.

13. The method of embodiment 11, wherein the trinucleotide repeat sequence has a GC content of at least 66%.

14. The method of embodiment 11, wherein the trinucleotide repeat sequence is selected from the group consisting of $(ACC)_n$, $(ACG)_n$, $(AGC)_n$, $(AGG)_n$, $(CAC)_n$, $(CAG)_n$, $(CCA)_n$, $(CCC)_n$, $(CCG)_n$, $(CCU)_n$, $(CGA)_n$, $(CGC)_n$, $(CGG)_n$, $(CGU)_n$, $(CUC)_n$, $(CUG)_n$, $(GAC)_n$, $(GAG)_n$, $(GCA)_n$, $(GCC)_n$, $(GCG)_n$, $(GCU)_n$, $(GGA)_n$, $(GGC)_n$, $(GGG)_n$, $(GGU)_n$, $(GUC)_n$, $(GUG)_n$, $(UCC)_n$, $(UCG)_n$, $(UGC)_n$, and $(UGG)_n$.

15. The method embodiment 11, wherein the trinucleotide repeat sequence is CAG or CUG and the trinucleotide repeat sequence is present in the guide strand.

16. The method of any of the foregoing embodiments, wherein the toxic RNA is a toxic shRNA/siRNA comprising a dsRNA sequence defined as follows:

```
05'- P01 P02 P03 P04 P05 P06 P07 P08 P09 P10 P11 P12 P13 P14 P15 P16 P17 P18 P19
      *   *   *   *   *   *   *   *   *   *   *   *   |   |   |   |   |   |   *
3'-  G19 G18 G17 G16 G15 G14 G13 G12 G11 G10 G09 G08 G07 G06 G05 G04 G03 G02 G01
``` wherein:

G01 through G19 and P01 through P19 are any ribonucleotide selected from A, U, G, and C, provided that:

G01 is A or U;

G02, G03, G04, G05, G06, and G07 are complementary to P18, P17, P16, P15, P14, and P13, respectively;

the percentage GC content of the region from G02 to G07 is 70-100%;

the percentage GC content of the region from G08 to G16 is 0-30%;

the percentage GC content of the region from G17 to G19 is 31-100%.

17. The method of embodiment 16, wherein the dsRNA is defined as follows:

```
5'-P01 P02 P03 P04 P05 P06 P07 P08 P09 P10 P11 P12 P13 P14 P15 P16 P17 P18 P19 P20 P21-3'
    *   *   *   *   *   *   *   *   *   *   *   |   |   |   |   |   |   *
3'-G21 G20 G19 G18 G17 G16 G15 G14 G13 G12 G11 G10 G09 G08 G07 G06 G05 G04 G03 G02 G01-5'
``` wherein:

G20, G21, P20, and P21 are any nucleotide.

18. The method of embodiment 16 or 17, wherein G02, G03, G04, G05, G06, and G07 comprise the sequence GGNNNN and N is any nucleotide.

19. The method of embodiment 18, wherein G02, G03, G04, G05, G06, and G07 have a GC content of greater than about 80%.

20. The method of embodiment 18, wherein G02, G03, G04, G05, G06, and G07 comprise the sequence NNNNNN, which is a polynucleotide sequence present in the 3' UTR of an mRNA for a tumor suppressor gene.

21. The method of embodiment 18, wherein the contiguous sequence of G02 through G07 is selected from the group consisting of GGGCAG, GGGGCU, GGGCUG, GGGCGA, GGGGGC, GGGGGU, GGGCGG, GGGUGG, GGUGGG, GGCUGG, GGGGCA, GGGGUC, GGCAGC, GAAGAU, GGUGGU, GGUGGA, GGGCAA, GGGCAU, GGAGGU, GGGGCC, GGGGCG, GUCUUC, GGAGCU, GGGAGA, GGGCGU, GGCGGU, GCAGGG, GGGAGU, CGGGGC, CUGGGC, GCAGGC, GGGCGC, GCUAAC, GGCGGG, GGGUGU, GGGUGC, GGGGGA, GAGGGU, GCGGGC, GUGGGC, GGGGUG, GGGAUC, GUAGUC, GACAGC, GCCUGU, GGUGCU, GGAGGA, GGGCCU, GCGGGG, GAGGGC, GGAUGC, GGGUGA, GCGGGU, UCUGGG, AGCUGG, GUGGGG, GGGCCG, GGAGGC, GGCUAU, CGUUGC, AGGGCC, GUUGCC, GAUGCU, GAGGGG, GUAGGC, GCUGGG, GUCUCC, AGUGGG, GGCUCU, GAAGUC, GUGGGU, GGCAGG, GGUGGC, GGCUAC, GCUAAU, GAUACC, GAUGCC, CCUGGG, GGGAGC, GAUGGC, CGGGUC, CGGGGG, UGGGGG, GUAGGU, GGGUAG, AGCGGC, GCGGCG, CGGGCC, CGCGGC, GUUUCC, GGCAUU, GGGGGG, GCUAGC, GCAGGU, GGGGAU, GGUGCC, GGCGGA, AGGCUC, ACAGAU, CCAUGG, AGUUGC, GGCUGC, ACUGGG, UGGCGG, GCGGUU, GGCGGC, GACAUC, GGGCUA, UGUAGU, GGAGCC, CCGACC, GGGCCA, GGGCUC, GGCGAU, AGGGGG, GGCCGG, AACAUC, GUCUGC, UGCCUG, GUCUCU, GUCCUC, CGUUCC, CUGGGA, GCGUGC, CGGGCU, GGCAGU, CGGGGU, GGUAGG, ACACCU, GUCAUC, GCCGGC, AGGGGC, GGCCUC, GGAGGG, GGUGUU, GGCAUG, UAUCCC, CGCCGC, AGGUGC, GACUGC, GCCUUC, AGGAGG, CGGAGG, GUCUGG, AGCUGC, GGCAUC, GCUGCU, CGGUGG, GUGUUC, GUCCAC, GGGCUU, GGCCGC, GGGUCU, GGCCGU, GGUAGU, ACAUCU, GCCGGU, AGCGGU, GGUUGG, AGGGUC, GGCUAG, AACCCC, GGUGAC, GUUGGG, GUAUCC, GGGGUU, GCUAUC, GGGGAG, CGGCGG, GAACUC, ACGGGC, GUAGGG, GGGUCC, CAGGCC, GGGAGG, GUUCAC, GGUGCG, ACAGGC, AGCGGG, ACAUGC, CAUGCU, CUUGGC, GUAGCU, CCGGGC, CGUAGC, GAAGCC, ACUUGG, GGCUCC, UGUAUC, GGCUUC, ACGACC, UCGGGC, GCCGAC, GGCUCA, GGCGAC, ACAGAC, CGGCUC, UCGUGC, GUUCCU, and GUCUGU.

22. The method of embodiment 16, wherein the toxic shRNA/siRNA is an shRNA illustrated as follows:

```
5'- P01 P02 P03 P04 P05 P06 P07 P08 P09 P10 P11 P12 P13 P14 P15 P16 P17 P18 P19-Lo
  *   *   *   *   *   *   *   *   *   *   *   *   |   |   |   |   |   |   *    )
3'- G19 G18 G17 G16 G15 G14 G13 G12 G11 G10 G09 G08 G07 G06 G05 G04 G03 G02 G01-po
``` wherein:

```
Lo
)
po
``` comprises a polynucleotide loop sequence.

23. Extracellular particles prepared by any of the foregoing embodiments.

24. A twenty-fourth embodiment includes extracellular particles comprising toxic RNA, optionally wherein the extracellular particles are exosomes.

25. The extracellular particles of embodiment 24, wherein the toxic RNA is a toxic shRNA/siRNA comprising a passenger strand, a guide strand, and a trinucleotide repeat sequence $(X_1X_2X_3)_n$ present in the passenger strand, the guide strand, or both strands, wherein $X_1$, $X_2$, and $X_3$ independently are selected from any ribonucleotide A, C, G, and U, and n is an integer from 3-10.

27. The extracellular particles of embodiment 25, wherein the trinucleotide repeat sequence has a GC content of at least 33%.

28. The extracellular particles of embodiment 25, wherein the trinucleotide repeat sequence has a GC content of at least 66%.

29. The extracellular particles of embodiment 25, wherein the trinucleotide repeat sequence is selected from the group consisting of $(ACC)_n$, $(ACG)_n$, $(AGC)_n$, $(AGG)_n$, $(CAC)_n$, $(CAG)_n$, $(CCA)_n$, $(CCC)_n$, $(CCG)_n$, $(CCU)_n$, $(CGA)_n$, $(CGC)_n$, $(CGG)_n$, $(CGU)_n$, $(CUC)_n$, $(CUG)_n$, $(GAC)_n$, $(GAG)_n$, $(GCA)_n$, $(GCC)_n$, $(GCG)_n$, $(GCU)_n$, $(GGA)_n$, $(GGC)_n$, $(GGG)_n$, $(GGU)_n$, $(GUC)_n$, $(GUG)_n$, $(UCC)_n$, $(UCG)_n$, $(UGC)_n$, and $(UGG)_n$.

30. The extracellular particles of embodiment 25, wherein the trinucleotide repeat sequence is CAG or CUG and the trinucleotide repeat sequence is present in the guide strand.

31. The extracellular particles of embodiment 24, wherein the toxic RNA is a toxic shRNA/siRNA comprising a dsRNA sequence defined as follows:

```
5'- P01 P02 P03 P04 P05 P06 P07 P08 P09 P10 P11 P12 P13 P14 P15 P16 P17 P18 P19
  *   *   *   *   *   *   *   *   *   *   *   *   |   |   |   |   |   |   *
3'- G19 G18 G17 G16 G15 G14 G13 G12 G11 G10 G09 G08 G07 G06 G05 G04 G03 G02 G01
``` wherein:
G01 through G19 and P01 through P19 are any ribonucleotide selected from A, U, G, and C, provided that:
G01 is A or U;
G02, G03, G04, G05, G06, and G07 are complementary to P18, P17, P16, P15, P14, and P13, respectively;
the percentage GC content of the region from G02 to G07 is 70-100%;
the percentage GC content of the region from G08 to G16 is 0-30%;
the percentage GC content of the region from G17 to G19 is 31-100%.

32. The extracellular particles of embodiment 31, wherein the dsRNA is defined as follows:

```
5'-P01 P02 P03 P04 P05 P06 P07 P08 P09 P10 P11 P12 P13 P14 P15 P16 P17 P18 P19 P20 P21-3'
    *   *   *   *   *   *   *   *   *   *   *   *   |   |   |   |   |   |   *
3'-G21 G20 G19 G18 G17 G16 G15 G14 G13 G12 G11 G10 G09 G08 G07 G06 G05 G04 G03 G02 G01-5'
``` wherein:
G20, G21, P20, and P21 are any nucleotide.

33. The extracellular particles of embodiment 31 or 32, wherein G02, G03, G04, G05, G06, and G07 comprise the sequence GGNNNN and N is any nucleotide.

34. The extracellular particles of embodiment 33, wherein G02, G03, G04, G05, G06, and G07 have a GC content of greater than about 80%.

35. The extracellular particles of embodiment 31, wherein G02, G03, G04, G05, G06, and G07 comprise the sequence NNNNNN, which is a polynucleotide sequence present in the 3' UTR of an mRNA for a tumor suppressor gene.

36. The extracellular particles of embodiment 31, wherein the contiguous sequence of G02 through G07 is selected from the group consisting of GGGCAG, GGGGCU, GGGCUG, GGGCGA, GGGGGC, GGGGGU, GGGCGG, GGGUGG, GGUGGG, GGCUGG, GGGGCA, GGGGUC, GGCAGC, GAAGAU, GGUGGU, GGUGGA, GGGCAA, GGGCAU, GGAGGU, GGGGCC, GGGGCG, GUCUUC, GGAGCU, GGGAGA, GGGCGU, GGCGGU, GCAGGG, GGGAGU, CGGGGC, CUGGGC, GCAGGC, GGGCGC, GCUAAC, GGCGGG, GGGUGU, GGGUGC, GGGGGA, GAGGGU, GCGGGC, GUGGGC, GGGGUG, GGGAUC, GUAGUC, GACAGC, GCCUGU, GGUGCU, GGAGGA, GGGCCU, GCGGGG, GAGGGC, GGAUGC, GGGUGA, GCGGGU, UCUGGG, AGCUGG, GUGGGG, GGGCCG, GGAGGC, GGCUAU, CGUUGC, AGGGCC, GUUGCC, GAUGCU, GAGGGG, GUAGGC, GCUGGG, GUCUCC, AGUGGG, GGCUCU, GAAGUC, GUGGGU, GGCAGG, GGUGGC, GGCUAC, GCUAAU, GAUACC, GAUGCC, CCUGGG, GGGAGC, GAUGGC, CGGGUC, CGGGGG, UGGGGG, GUAGGU, GGGUAG, AGCGGC, GCGGCG, CGGGCC, CGCGGC, GUUUCC, GGCAUU, GGGGGG, GCUAGC, GCAGGU, GGGGAU, GGUGCC, GGCGGA, AGGCUC, ACAGAU, CCAUGG, AGUUGC, GGCUGC, ACUGGG, UGGCGG, GCGGUU, GGCGGC, GACAUC, GGGCUA, UGUAGU, GGAGCC, CCGACC, GGGCCA, GGGCUC, GGCGAU, AGGGGG, GGCCGG, AACAUC, GUCUGC, UGCCUG, GUCUCU, GUCCUC, CGUUCC, CUGGGA, GCGUGC, CGGGCU, GGCAGU, CGGGGU, GGUAGG, ACACCU, GUCAUC, GCCGGC, AGGGGC, GGCCUC, GGAGGG, GGUGUU, GGCAUG, UAUCCC, CGCCGC, AGGUGC, GACUGC, GCCUUC, AGGAGG, CGGAGG, GUCUGG, AGCUGC, GGCAUC, GCUGCU, CGGUGG, GUGUUC, GUCCAC, GGGCUU, GGCCGC, GGGUCU, GGCCGU, GGUAGU, ACAUCU, GCCGGU, AGCGGU, GGUUGG, AGGGUC, GGCUAG, AACCCC, GGUGAC, GUUGGG, GUAUCC, GGGGUU, GCUAUC, GGGGAG, CGGCGG, GAACUC, ACGGGC, GUAGGG, GGGUCC, CAGGCC, GGGAGG, GUUCAC, GGUGCG, ACAGGC, AGCGGG, ACAUGC, CAUGCU, CUUGGC, GUAGCU, CCGGGC, CGUAGC, GAAGCC, ACUUGG, GGCUCC, UGUAUC, GGCUUC, ACGACC, UCGGGC, GCCGAC, GGCUCA, GGCGAC, ACAGAC, CGGCUC, UCGUGC, GUUCCU, and GUCUGU.

37. The extracellular particles of embodiment 31, wherein the toxic shRNA/siRNA is an shRNA illustrated as follows:

```
5'- P01 P02 P03 P04 P05 P06 P07 P08 P09 P10 P11 P12 P13 P14 P15 P16 P17 P18 P19-Lo
     *   *   *   *   *   *   *   *   *   *   *   |   |   |   |   |   |   *     )
3'- G19 G18 G17 G16 G15 G14 G13 G12 G11 G10 G09 G08 G07 G06 G05 G04 G03 G02 G01-po
``` wherein:

$$L_0 ) p_0$$

comprises a polynucleotide loop sequence.

38. A pharmaceutical compositions comprising the extracellular particles of any of embodiments 23-37 and a pharmaceutical carrier, diluent, or excipient.

39. A method for treating a disease or disorder in a subject in need thereof, the method comprising administering to the subject the pharmaceutical composition of embodiment 38.

40. The method of embodiment 39, wherein the disease or disorder is a cell proliferative disease or disorder such as cancer.

EXAMPLES

The following examples are illustrative and should not be interpreted to limit the scope of the claimed subject matter.

Title—Producing Super Toxic shRNAs in Cells

Background

RNA interference (RNAi) is a form of post-transcriptional regulation exerted by 19-21 nt long double stranded RNAs that negatively regulate gene expression at the mRNA level. RNAi-active guide RNAs can come from endogenous siRNAs and micro(mi)RNAs. For a miRNA, the RNAi pathway begins in the nucleus with transcription of a primary miRNA precursor (pri-miRNA) (1). Pri-miRNAs are first processed by the Drosha/DGCR8 microprocessor complex into pre-miRNAs (2), which are then exported from the nucleus to the cytoplasm by Exportin 5 (3). Once in the cytoplasm, Dicer processes them further (4, 5) and these mature dsRNA duplexes are then loaded into Argonaute (Ago) proteins to form the RNA-induced silencing complex (RISC) (6). The sense/passenger strand is ejected/degraded, while the guide strand remains associated with the RISC (7). Depending on the degree of complementarity between the guide strand and its target, the outcome of RNAi can either be target degradation—most often achieved by siRNAs with full complementarity to their target mRNA (8)—or miRNA-like cleavage-independent silencing, mediated by deadenylation/degradation or translational repression (9). The latter mechanism can be initiated with as little as six nucleotide base-pairing between a guide RNA's so-called seed sequence (positions 2 to 7) and fully complementary seed matches in the target RNA (10, 11). This seed-based targeting most often occurs in the 3'UTR of a target mRNA (12, 13).

A number of miRNAs function either as tumor suppressors or as oncogenes (14). Their cancer specific activities are usually explained by their identified targets, being oncogenes or tumor suppressors, respectively (14). Examples of targets of tumor-suppressive miRNAs are the oncogenes Bcl-2 for miR-15/16 (15) and c-Myc for miR-34a (16). While many miRNAs have been reported to have both tumor suppressive and oncogenic activities depending on the cancer context, examples for widely established tumor promoting miRNAs are miR-221/222, miR-21, miR-155, and members of the miR-17-92 cluster, or its paralogues miR-106b~25 and miR-106a~363 (17, 18). In contrast, two of the major tumor suppressive miRNA families are miR-15/16 and the p53 regulated miR-34a/c and miR-34b (19).

We recently discovered that many si- and shRNAs can kill all tested cancer cell lines through RNAi by targeting the 3'UTRs of critical survival genes (20). We demonstrated that siRNA killed the cells through RNAi by showing that knockdown of AGO2 severely blunted the toxicity induced by either si- or shRNAs (20). In addition, toxic shRNAs were not toxic anymore when introduce into cells lacking Dicer expression as Dicer is required for processing of shRNAs (20).

We called this cell death mechanism DISE (for death induced by survival gene elimination). Cancer cells have difficulty developing resistance to this mechanism both in vitro and when treated in vivo (21). We reported that a 6mer seed sequence in the toxic siRNAs is sufficient for effective killing (20). We recently performed a strand specific siRNA screen with a library of individual siRNAs representing all 4096 possible 6mer seed sequences in a neutral RNA duplex. This screen, while based on siRNA biochemistry was not designed to identify targets that are degraded through siRNA mediated slicing activity but to identify toxicity caused by moderately targeting hundreds of genes required for cell survival in a mechanism similar to miRNA-induced silencing.

We found that the most toxic 6mer seeds are G-rich with a G enrichment towards the 5' end targeting survival genes with a high C content in their 3'UTR in a miRNA-like manner. The top 200 most toxic seeds had the consensus GGGGGC (22). Many tumor suppressive miRNAs such as miR-34a-5p but none of the established oncogenic miRNAs contain G-rich 6mer seeds and most of miR-34a-5p's toxicity comes from its 6mer seed sequence. Consistently, we demonstrate that for most miRNAs the more abundant mature form corresponds to the arm that contains the less toxic seed. In contrast, for major tumor suppressive miRNAs, the mature miRNA is derived from the arm that harbors the more toxic seed.

We found that normal cells are quite efficiently protected from this form of cell death by the expression of large amounts of RISC bound miRNAs that carry nontoxic seeds (20, 23, 24) (they have to, otherwise normal cells most of which express large amounts of miRNAs would die). When we discovered DISE and found evidence that it could be a fundamental anti-cancer mechanism developed during evolution, we wondered whether there could be patients with a disease in which this mechanism was hyperactive. We predicted that this would result in degeneration of certain tissues and these patients would be expected to have lower cancer incidence. In addition, the disease had to involve a RNA component, preferentially even an RNAi component. We found these criteria were met in a number of trinucleotide repeat (TNR) expansion diseases. One of the TNR diseases, Huntington's disease (HD), stood out. HD is caused by the expansion of a CAG repeat in the gene huntingtin (HTT) (reviewed in (25)). When the repeat expansion in HTT exceeds a certain tolerated length, patients suffer from loss of neurons in a specific part of the brain resulting in a debilitating terminal neurodegenerative disorder. Furthermore, four independent studies reported an inverse correlation between the repeat length and the incidence of multiple cancers in HD patients. Finally, the CAG repeats in the HTT gene have been shown to be processed to small RNA active siRNAs (discussed in (23, 25)). In summary, HD and many other TNR diseases met the criteria of having an overactive anti-cancer mechanism. But could the CAG repeat sequences present in these patients be used to treat cancer? To test this, we designed siRNA duplexes based on the CAG repeat (present in HD patients) and the complementary CUG repeat (expanded in muscular dystrophy type I patients). Remarkably, these siRNAs killed all tested human and mouse cancer cell lines at very low concentrations (as low as 10 pM (23)). They were therefore 100-1000 times more toxic than any DISE inducing siRNA we had tested. To determine whether there was something special about CAG or CUG repeats we performed another screen testing all possible 60 trinucleotide repeat-based siRNAs. The only ones that were toxic to all cells were all siRNAs based on CAG and the complementary CUG TNR (23). We then provided evidence that the repeat-based siRNAs kill cancer cells by targeting genes that are critical for cell survival and contain repeat sequences themselves that are complementary to the toxic TNR-based siRNAs. TNR-based siRNAs therefore kill cancer cells by targeting the CDS of certain survival genes in a mechanism that is different from the DISE mechanism described above.

We recently developed a model of how TNR expansion sequences embedded in the genome of higher organisms could be part of an anti-cancer mechanism that we can now use to develop a new form of cancer therapy (25). In summary, we now have two different types of toxic small RNAs that kill cancer cells through RNAi in a miRNA-like fashion: 1) si/sh/miRNAs that kill the cells through 6mer seed toxicity by targeting the 3'UTR of hundreds of survival genes and 2) TNR based siRNAs that kill cells by targeting multiple survival genes through siRNA like-targeting of complete complementary repeat regions present in the ORF of the targeted genes.

The Problem

To use the toxic si/sh/miRNAs for treatment of cancer there are multiple ways of delivering the RNAs to the cancer cells. One way is to have cells express the toxic sh/siRNAs/miRNAs and package the cellular content into extracellular vesicles that can be used for treatment. Another way is to have viruses express the toxic shRNAs/miRNAs which could then be used to treat cancer. In both cases it is difficult to generate cells that express large quantities of super toxic shRNAs or cells that would generate viruses that harbor super toxic shRNAs as in both cases the cells producing the shRNA or the virus could die by DISE. This would result in very low yields of toxic reagents.

The Invention that Addresses this Problem

This invention will now allow expression of super toxic shRNAs and siRNAs in cells resistant to this form of cell death which can then be used to package the cytosolic content into exosomes. To prevent the producing cells from being killed by the super toxic shRNAs, we infected cells lacking either Dicer or Ago2, which cannot process shRNAs to mature siRNAs or cannot execute RNAi, respectively. These mutant cells are resistant to the effects of the introduced sh- or siRNA, respectively. The Ago2 k.o. cells can be used to produce large quantities of shRNAs in cells or load cells with large quantities of toxic siRNAs. The Dicer k.o. cells can be used to generate large quantities of toxic shRNAs. As the Dicer k.o. cells are resistant to expressed toxic shRNAs they will also allow to produce viruses carrying toxic shRNAs in large quantities. As a proof of principle we demonstrate that total RNA isolated from Dicer k.o. cells after inducing expression of a highly toxic shRNA can kill wild-type cells when transfected in a dose dependent manner. These cells can now be used to produce extracellular vesicles such as exosomes.

DESCRIPTION OF INVENTION

To test whether cells deficient for either AGO2 or Dicer would tolerate high amounts of toxic small RNAs and to determine to what extent the toxicity was mediated by RNAi, we tested HeLa cells described to be deficient for AGO2 (26), and 293T cells described to lack expression of either AGO2 (27) or Dicer (28). In a Western blot analysis both the HeLa and the 293T cells in which Ago2 had been knocked out through CRIPSR/Cas9 editing a residual amount of AGO2 proteins was detectable with an apparent compensatory upregulation of AGO1 (FIG. 1A, left) pointing at a critical survival function of Ago2 for these cells. These cells would now be expected to be severely impaired to mediate canonical RNAi induced by siRNAs completely complementary to their targets as this requires the slicing activity of AGO2 in the RISC. In contrast miRNA like gene silencing mediated by partial complementarity with only the seed sequences being completely complementary should still be functional as this only requires AGO1 (29). In contrast, two Dicer k.o. clones of 293T cells were found to be completely deficient in Dicer expression (FIG. 1A, right). These cells were expected to be fully sensitive to toxic siRNAs but resistant to toxic shRNAs as they cannot process shRNAs to active siRNAs that get loaded into the RISC.

To test the sensitivity of the different cell lines to different toxic si- and shRNAs, we used the following toxic small RNAs (all transfected at 10 nM): a non toxic control siRNA (siNT1, (22)), a number of toxic siRNAs that kill cells through a miRNA like mechanism. These include the Fas ligand (FasL) derived toxic siL3 (21), si34aSeed, which contains the toxic 6mer seed of the miRNA miR-34a-5p (22), and a siRNA we generated by converting a highly toxic FasL targeting shRNA (shL3) into an siRNA (sh→siL3, (20)). In addition, we tested siCAG/CUG, a super toxic siRNA that is based on sequences found in mutant genes in trinucleotide repeat expansion diseases, such as Huntington's disease (HD) or Spinal Bulbar Muscular Atrophy (SBMA). siCAG/CUG kills all cells by targeting through complete complementarity to endogenous genes that carry repeat sequences in their open reading frame (23). This form of RNAi is expected to be completely dependent on the presence of AGO2. To test the performance of a toxic hairpin that would require processing by Dicer to gain activity, we designed a hairpin that contains the CAG repeat sequence found in the androgen receptor (AR) that causes SBMA (FIG. 1B) (25). This structure was modeled after a report that described formation of a CAG hairpin that is stabilized at its end by a complementary repeat region that is located adjacent to the CAG repeat sequences present in the AR gene (30). To gain toxicity this structure would need to be processed by Dicer.

We first tested the toxic activities of various siRNAs on cells lacking either AGO2 or Dicer (FIG. 1C, D). In all cases we used growth reduction as a surrogate marker for cell death as we described in multiple publications that in all cases DISE is characterized by growth reduction followed by cell death (20, 22, 23, 31, 32). While parental HeLa cells were susceptible to the toxicity of the toxic si34Seed and even more so to the super toxic siCAG/CUG, cells lacking AGO2 expression were much less sensitive to this toxicity (FIG. 1C). siCAG/CUG was most affected by the absence of AGO2 as it acts through complete complementarity causing AGO2 mediated mRNA target degradation. In contrast, si34Seed was only slightly less toxic as it functions mostly through translational silencing for which AGO1 is sufficient. 293T cells were tested with two siRNAs.

Both si34aSeed and siL3 showed only a moderate growth inhibition in parental 293T cells. In contrast two Dicer k.o. clones were super susceptible to the toxic effects of both siRNAs (FIG. 1D). This result confirms that Dicer activity is not required for two siRNAs to be toxic. On the contrary in the absence of Dicer and most noncanonical miRNAs cell become hypersensitive to DISE. We had interpreted this effect originally seen in Dicer deficient HCT116 cells and now confirmed in 293T cells by large quantities of nontoxic miRNAs protecting cells from DISE (20, 22-24).

Finally, we tested the activity of a toxic hairpin (HP) on cells lacking either AGO2 or Dicer (FIG. 1E). Both the AR CAG derived hairpin we had constructed and sh→siL3 were highly toxic to parental 293T cells. In contrast, in the 293T cells lacking AGO2 expression, the AR derived HP showed no toxicity anymore confirming that is acts through AGO2. Interestingly, sh→siL3 was still highly toxic suggesting that it kills cells through a efficient silencing that involves Ago proteins other than AGO2, presumably AGO1. As expected sh→siL3 does not require Dicer for activity, however, the toxic activity of AR HP was severely blunted in the absence of Dicer suggesting that Dicer is processing AR HP. These experiments suggest that it should be possible to express any toxic hairpin structured shRNA in either Ago2 or Dicer k.o. cells without killing them.

Figure 2:
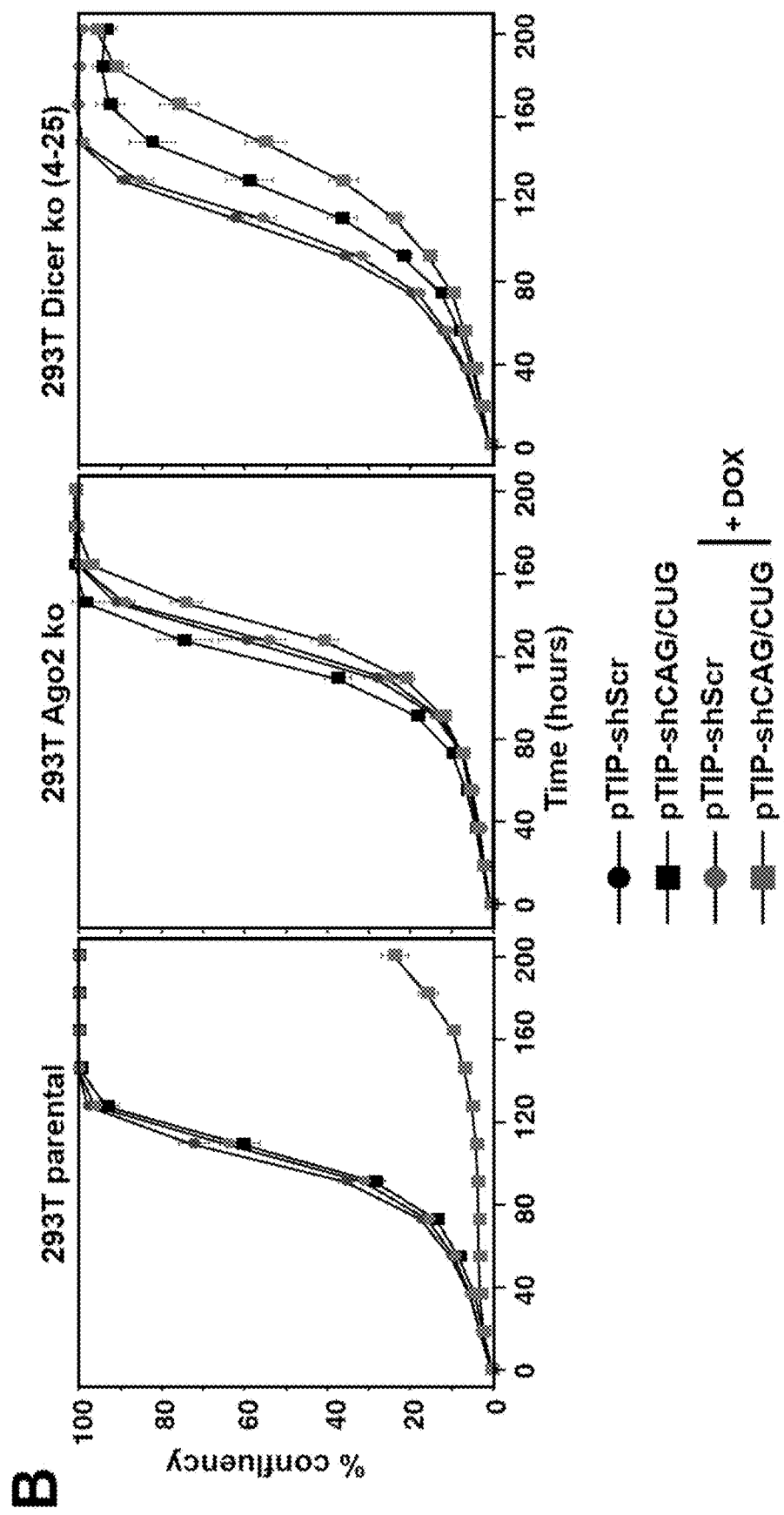
FIG. 2. Inducible expression of shScr and shCAG/CUG in wt, Ago2 and Dicer k.o. cells. (A) Structure of the shRNA produced by the pTIP-shCAG/CUG shRNA (SEQ ID NO: 4). (B) Cell confluency over time of the indicated cells expressing either pTIP-shScr or pTIP-shCAG/CUG cultured in the absence or presence of 0.1 μg/ml DOX.

To produce large quantities of toxic shRNAs in DISE resistant cells, we cloned the super toxic siRNA siCAG/CUG into the Tet inducible lentiviral vector pTIP (20) (FIG. 2A). Based on our small RNA Seq analysis of similar pTIP based shRNAs we expected Dicer to cleave this shRNA mainly at the indicated sites (arrow heads in FIG. 2A). 293T wt, AGO2 and Dicer k.o. cells were stably infected with this lentivirus and cultured in the absence or presence of 0.1 µg/ml of Doxycycline to induce expression of the shRNAs. Cells infected with pTIP-shScr (a non toxic control shRNA) were also tested. In the parental cells addition of Dox to the cells expressing pTIP-shCAG/CUG led to robust cell death induction (FIG. 2B, left). In contrast, neither in the AGO2 or the Dicer k.o. cells did this lead to induction of substantial cell death (FIG. 2B, center and right panel). These data suggest that it should be possible to express large quantities of super toxic shRNAs such as shCAG/CUG in cells lacking either AGO2 or Dicer.

Figure 3:
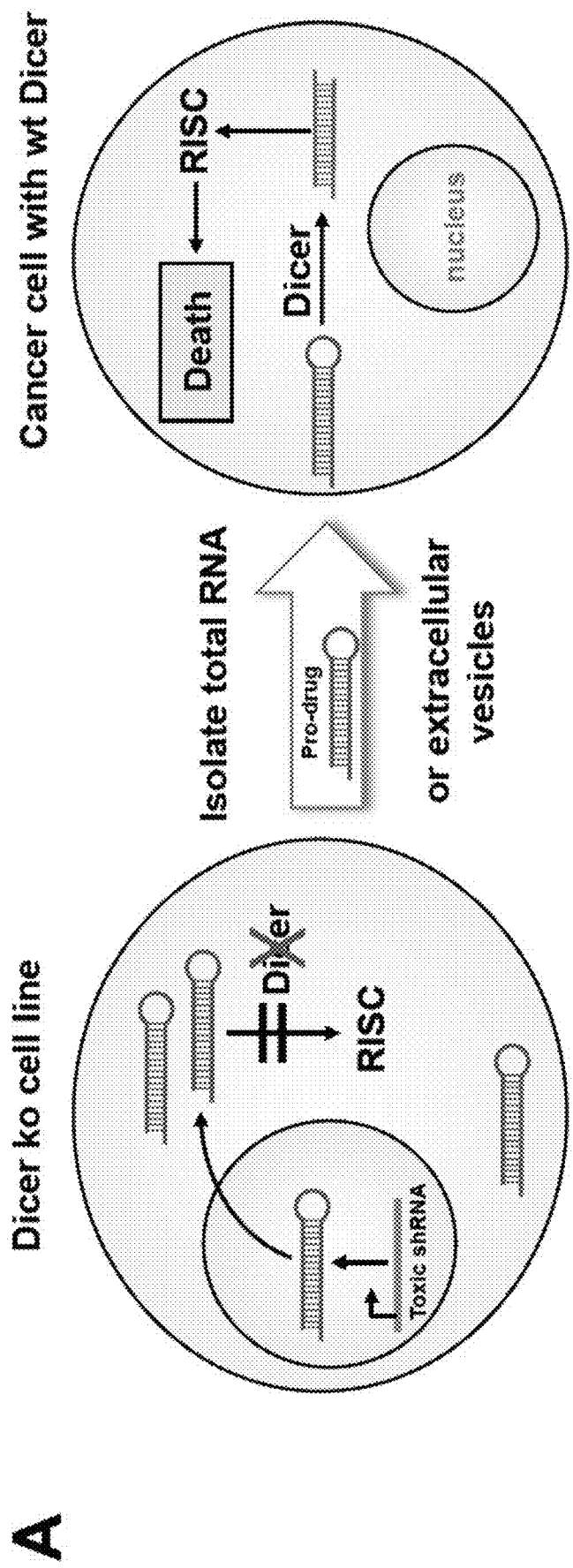
FIG. 3. Transfection of HeyA8 cells with different doses of total RNA isolated from shScr and shCAG/CUG expressing Dicer k.o. 293T cells. (A) Scheme to illustrate the expression of toxic shRNAs in Dicer k.o. cells and transfer for cell produced toxic shRNA ("pro-drug") to Dicer wt target cells that will die after taking up the non toxic pro-drug and with the help of Dicer converted to a highly toxic shRNA that will enter the RISC and kill the cell. (B)
Figure 3:
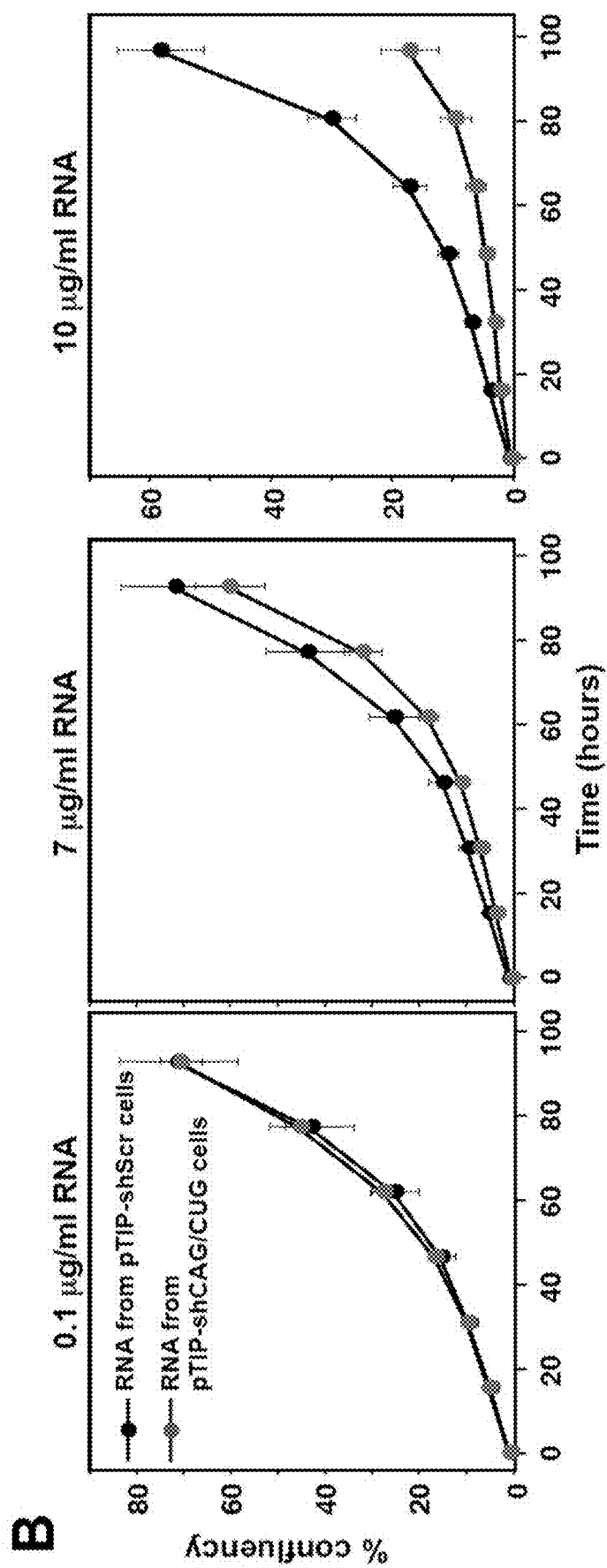

Due to the repetitive nature of the shRNA we were not able to confirm the expression of the unprocessed shCAG/CUG in the resistant cells by PCR (data not shown). We therefore decided to test this in a functional assay which also served as a proof-of-concept that shRNAs expressed in resistant cells can be isolated to kill other cancer cells which always express at least one allele of Dicer (FIG. 3A).

Complete loss of Dicer has never been described in cancer. And here is the likely reason why (extracts from published work): "Although mutations in DICER (often resulting in truncations or a reduction in DICER expression) are commonly seen in many cancers, loss of heterozygosity (LOH) resulting in complete deficiency of DICER function is extremely rare. Mutational analyses of human cancers indicate that, while partial loss of DICER is associated with many cancers, its complete loss is not well tolerated". (33). "A pivotal study by Tyler Jacks's group demonstrated that shRNA-mediated downregulation of Dicer resulted in enhanced cellular transformation and tumorigenesis in mouse lung adenocarcinoma cells (34). Subsequently, Dicer heterozygous mice were shown to exhibit increased tumor burden and reduced survival in K-Ras-driven mouse models of lung cancer and sarcoma (35)". Most interestingly, while loss of a single allele of Dicer enhanced tumorigenesis, loss of both copies of Dicer had the opposite effect. Indeed, it was rare to find tumors that had lost both copies of Dicer, and enforced complete deletion of Dicer led to inhibition of tumorigenesis."

The reason Dicer cannot be deleted may be because it is wired to play a role in DNA damage repair. Tumors completely lacking Dicer would accumulate significant DNA damage resulting in cell death (36). All these publications suggest that delivery of a toxic Dicer shRNA that requires Dicer processing will always kill all cancer cells that cannot delete Dicer.

REFERENCES

1. Lee Y, Kim M, Han J, Yeom K H, Lee S, Baek S H, Kim V N. (2004). MicroRNA genes are transcribed by RNA polymerase II. EMBO J. 23:4051-60.
2. Han J, Lee Y, Yeom K H, Kim Y K, Jin H, Kim V N. (2004). The Drosha-DGCR8 complex in primary microRNA processing. Genes Dev. 18:3016-27.
3. Yi R, Qin Y, Macara I G, Cullen B R. (2003). Exportin-5 mediates the nuclear export of pre-microRNAs and short hairpin RNAs. Genes Dev. 17:3011-6.
4. Bernstein E, Caudy A A, Hammond S M, Hannon G J. (2001). Role for a bidentate ribonuclease in the initiation step of RNA interference. Nature. 409:363-6.
5. Hutvagner G, McLachlan J, Pasquinelli A E, Balint E, Tuschl T, Zamore P D. (2001). A cellular function for the RNA-interference enzyme Dicer in the maturation of the let-7 small temporal RNA. Science. 293:834-8.
6. Wang Y, Sheng G, Juranek S, Tuschl T, Patel D J. (2008). Structure of the guide-strand-containing argonaute silencing complex. Nature. 456:209-13.
7. Leuschner P J, Ameres S L, Kueng S, Martinez J. (2006). Cleavage of the siRNA passenger strand during RISC assembly in human cells. EMBO Rep. 7:314-20.
8. Schirle N T, MacRae I J. (2012). The crystal structure of human Argonaute2. Science. 336:1037-40.
9. Eulalio A, Huntzinger E, Izaurralde E. (2008). GW182 interaction with Argonaute is essential for miRNA-mediated translational repression and mRNA decay. Nat Struct Mol Biol. 15:346-53.
10. Lewis B P, Shih I H, Jones-Rhoades M W, Bartel D P, Burge C B. (2003). Prediction of mammalian microRNA targets. Cell. 115:787-98.
11. Lai E C. (2002). Micro RNAs are complementary to 3' UTR sequence motifs that mediate negative post-transcriptional regulation. Nat Genet. 30:363-4.
12. Selbach M, Schwanhausser B, Thierfelder N, Fang Z, Khanin R, Rajewsky N. (2008). Widespread changes in protein synthesis induced by microRNAs. Nature. 455: 58-63.
13. Baek D, Villen J, Shin C, Camargo F D, Gygi S P, Bartel D P. (2008). The impact of microRNAs on protein output. Nature. 455:64-71.
14. Esquela-Kerscher A, Slack F J. (2006). Oncomirs—microRNAs with a role in cancer. Nat Rev Cancer. 6:259-69.
15. Balatti V, Pekarky Y, Rizzotto L, Croce C M. (2013). miR deregulation in CLL. Adv Exp Med Biol. 792:309-25.
16. Slabakova E, Culig Z, Remsik J, Soucek K. (2017). Alternative mechanisms of miR-34a regulation in cancer. Cell Death Dis. 8:e3100.
17. Hua Y J, Larsen N, Kalyana-Sundaram S, Kjems J, Chinnaiyan A M, Peter M E. (2013). miRConnect 2.0: Identification of antagonistic, oncogenic miRNA families in three human cancers. BMC Genomics. 14:179.
18. Concepcion C P, Bonetti C, Ventura A. (2012). The microRNA-17-92 family of microRNA clusters in development and disease. Cancer journal. 18:262-7.

19. He X, He L, Hannon G J. (2007). The guardian's little helper: microRNAs in the p53 tumor suppressor network. Cancer Res. 67:11099-101.
20. Putzbach W, Gao Q Q, Patel M, van Dongen S, Haluck-Kangas A, Sarshad A A, Bartom E, Kim K Y, Scholtens D M, Hafner M, Zhao J C, Murmann A E, Peter M E. (2017). Many si/shRNAs can kill cancer cells by targeting multiple survival genes through an off-target mechanism. eLife. 6: e29702.
21. Murmann A E, McMahon K M, Halluck-Kangas A, Ravindran N, Patel M, Law C, Brockway S, Wei J J, Thaxton C S, Peter M E. (2017). Induction of DISE in ovarian cancer cells in vivo. Oncotarget. 8:84643-58.
22. Gao Q Q, Putzbach W, Murmann A E, Chen S, Ambrosini G, Peter J M, Bartom E, Peter M E. (2018). 6mer seed toxicity in tumor suppressive miRNAs. Nature Comm. 9:4504.
23. Murmann A E, Gao Q Q, Putzbach W T, Patel M, Bartom E T, Law C Y, Bridgeman B, Chen S, McMahon K M, Thaxton C S, Peter M E. (2018). Small interfering RNAs based on huntingtin trinucleotide repeats are highly toxic to cancer cells. EMBO Rep. 19:e45336.
24. Putzbach W, Gao Q Q, Patel M, Haluck-Kangas A, Murmann A E, Peter M E. (2018). DISE—A Seed Dependent RNAi Off-Target Effect that Kills Cancer Cells. Trends in Cancer. 4:10-9.
25. Murmann A E, Yu J, Opal P, Peter M E. (2018). Trinucleotide repeat expansion diseases, RNAi and cancer. Trends in Cancer. 4:684-700.
26. Eckenfelder A, Segeral E, Pinzon N, Ulveling D, Amadori C, Charpentier M, Nidelet S, Concordet J P, Zagury J F, Paillart J C, Berlioz-Torrent C, Seitz H, Emiliani S, Gallois-Montbrun S. (2017). Argonaute proteins regulate HIV-1 multiply spliced RNA and viral production in a Dicer independent manner. Nucleic Acids Res. 45:4158-73.
27. van Eijl R, van den Brand T, Nguyen L N, Mulder K W. (2017). Reactivity of human AGO2 monoclonal antibody 11A9 with the SWI/SNF complex: A case study for rigorously defining antibody selectivity. Sci Rep. 7:7278.
28. Bogerd H P, Whisnant A W, Kennedy E M, Flores O, Cullen B R. (2014). Derivation and characterization of Dicer- and microRNA-deficient human cells. RNA. 20:923-37.
29. Yang J S, Lai E C. (2011). Alternative miRNA biogenesis pathways and the interpretation of core miRNA pathway mutants. Mol Cell. 43:892-903.
30. de Mezer M, Wojciechowska M, Napierala M, Sobczak K, Krzyzosiak W J. (2011). Mutant CAG repeats of Huntingtin transcript fold into hairpins, form nuclear foci and are targets for RNA interference. Nucleic Acids Res. 39:3852-63.
31. Putzbach W, Haluck-Kangas A, Gao Q Q, Sarshad A A, Bartom E T, Stults A, Qadir A S, Hafner M, Peter M E. (2018). CD95/Fas ligand mRNA is toxic to cells. eLife. 7:e38621.
32. Patel M, Peter M E. (2018). Identification of DISE-inducing shRNAs by monitoring cellular responses. Cell Cycle. 17: 506-14.
33. Foulkes W D, Priest J R, Duchaine T F. (2014). DICER1: mutations, microRNAs and mechanisms. Nat Rev Cancer. 14:662-72.
34. Kumar M S, Lu J, Mercer K L, Golub T R, Jacks T. (2007). Impaired microRNA processing enhances cellular transformation and tumorigenesis. Nat Genet. 39:673-7.
35. Kumar M S, Pester R E, Chen C Y, Lane K, Chin C, Lu J, Kirsch D G, Golub T R, Jacks T. (2009). Dicer1 functions as a haploinsufficient tumor suppressor. Genes Dev. 23:2700-4.
36. Swahari V, Nakamura A, Baran-Gale J, Garcia I, Crowther A J, Sons R, Gershon T R, Hammond S, Sethupathy P, Deshmukh M. (2016). Essential Function of Dicer in Resolving DNA Damage in the Rapidly Dividing Cells of the Developing and Malignant Cerebellum. Cell Rep. 14:216-24.
37. Ingato D, Edson J A, Zakharian M, Kwon Y J. (2018). Cancer Cell-Derived, Drug-Loaded Nanovesicles Induced by Sulfhydryl-Blocking for Effective and Safe Cancer Therapy. ACS nano. 12:9568-77.
38. Wang Q, Yu J, Kadungure T, Beyene J, Zhang H, Lu Q. (2018). ARMMs as a versatile platform for intracellular delivery of macromolecules. Nat Commun. 9:960.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A method for producing extracellular particles comprising a double-stranded RNA (dsRNA) polynucleotide, the dsRNA polynucleotide comprising a passenger strand and a guide strand that form a duplex, wherein the passenger strand comprises a trinucleotide repeat sequence $(CUG)_n$, wherein n is an integer from 3-10; (ii) the guide strand comprises a trinucleotide repeat sequence $(CAG)_n$, wherein n is an integer from 3-10; and (iii) the $(CUG)_n$ and $(CAG)_n$ trinucleotide repeat sequence hybridize to each, and the dsRNA polynucleotide induces death by survival gene elimination (DISE) in a human cell after the RNA is expressed in the human cell and the RNA is processed for RNA interference (RNAi) and RNAi is executed, the method comprising:
  (a) expressing the dsRNA polynucleotide in a eukaryotic cell that is deficient in a gene selected from Dicer, AGO2, and both of Dicer and AGO2, wherein the expressed dsRNA polynucleotide does not induce cell death in the eukaryotic cell; and
  (b) isolating the extracellular particles comprising the dsRNA polynucleotide from the eukaryotic cell.

2. The method of claim 1, wherein the dsRNA polynucleotide is shRNA, siRNA, pre-miRNA, or miRNA.

3. The method of claim 1, wherein the eukaryotic cell has been engineered to be deficient in the Dicer gene and/or the eukaryotic cell has been engineered to not express the Dicer protein.

4. The method of claim 1, wherein the eukaryotic cell has been engineered to be deficient in the AGO2 and/or the eukaryotic cell has been engineered to not express the AGO2 protein.

5. The method of claim 1, wherein the method comprises expressing a shRNA or a pre-miRNA in the cell via transfecting or infecting the cell with a vector that expresses the shRNA or the pre-miRNA.

6. The method of claim 5, wherein the vector comprises an inducible promoter for expressing the shRNA or the pre-miRNA.

7. The method of claim 6, wherein the vector is a viral vector.

* * * * *

SEQUENCE LISTING

```
<160> NUMBER OF SEQ ID NOS: 4

<210> SEQ ID NO 1
<211> LENGTH: 1922
<212> TYPE: PRT
<213> ORGANISM: Homo sapiens
```

<400> SEQUENCE: 1

```
Met Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
            20                  25                  30

Gln Gln Glu Ala Ile His Asp Asn Ile Tyr Thr Pro Arg Lys Tyr Gln
        35                  40                  45

Val Glu Leu Leu Glu Ala Ala Leu Asp His Asn Thr Ile Val Cys Leu
    50                  55                  60

Asn Thr Gly Ser Gly Lys Thr Phe Ile Ala Val Leu Leu Thr Lys Glu
65                  70                  75                  80

Leu Ser Tyr Gln Ile Arg Gly Asp Phe Ser Arg Asn Gly Lys Arg Thr
                85                  90                  95

Val Phe Leu Val Asn Ser Ala Asn Gln Val Ala Gln Gln Val Ser Ala
            100                 105                 110

Val Arg Thr His Ser Asp Leu Lys Val Gly Glu Tyr Ser Asn Leu Glu
        115                 120                 125

Val Asn Ala Ser Trp Thr Lys Glu Arg Trp Asn Gln Glu Phe Thr Lys
    130                 135                 140

His Gln Val Leu Ile Met Thr Cys Tyr Val Ala Leu Asn Val Leu Lys
145                 150                 155                 160

Asn Gly Tyr Leu Ser Leu Ser Asp Ile Asn Leu Leu Val Phe Asp Glu
                165                 170                 175

Cys His Leu Ala Ile Leu Asp His Pro Tyr Arg Glu Ile Met Lys Leu
            180                 185                 190

Cys Glu Asn Cys Pro Ser Cys Pro Arg Ile Leu Gly Leu Thr Ala Ser
        195                 200                 205

Ile Leu Asn Gly Lys Cys Asp Pro Glu Glu Leu Glu Lys Ile Gln
    210                 215                 220

Lys Leu Glu Lys Ile Leu Lys Ser Asn Ala Glu Thr Ala Thr Asp Leu
225                 230                 235                 240

Val Val Leu Asp Arg Tyr Thr Ser Gln Pro Cys Glu Ile Val Val Asp
                245                 250                 255

Cys Gly Pro Phe Thr Asp Arg Ser Gly Leu Tyr Glu Arg Leu Leu Met
            260                 265                 270

Glu Leu Glu Glu Ala Leu Asn Phe Ile Asn Asp Cys Asn Ile Ser Val
        275                 280                 285

His Ser Lys Glu Arg Asp Ser Thr Leu Ile Ser Lys Gln Ile Leu Ser
    290                 295                 300

Asp Cys Arg Ala Val Leu Val Val Leu Gly Pro Trp Cys Ala Asp Lys
305                 310                 315                 320

Val Ala Gly Met Met Val Arg Glu Leu Gln Lys Tyr Ile Lys His Glu
                325                 330                 335

Gln Glu Glu Leu His Arg Lys Phe Leu Leu Phe Thr Asp Thr Phe Leu
            340                 345                 350

Arg Lys Ile His Ala Leu Cys Glu Glu His Phe Ser Pro Ala Ser Leu
        355                 360                 365

Asp Leu Lys Phe Val Thr Pro Lys Val Ile Lys Leu Leu Glu Ile Leu
    370                 375                 380

Arg Lys Tyr Lys Pro Tyr Glu Arg Gln Gln Phe Glu Ser Val Glu Trp
385                 390                 395                 400

Tyr Asn Asn Arg Asn Gln Asp Asn Tyr Val Ser Trp Ser Asp Ser Glu
                405                 410                 415
```

```
Asp Asp Asp Glu Asp Glu Ile Glu Lys Glu Lys Pro Glu Thr
            420             425             430

Asn Phe Pro Ser Pro Phe Thr Asn Ile Leu Cys Gly Ile Phe Val
        435             440             445

Glu Arg Arg Tyr Thr Ala Val Val Leu Asn Arg Leu Ile Lys Glu Ala
    450             455             460

Gly Lys Gln Asp Pro Glu Leu Ala Tyr Ile Ser Ser Asn Phe Ile Thr
465             470             475             480

Gly His Gly Ile Gly Lys Asn Gln Pro Arg Asn Lys Gln Met Glu Ala
                485             490             495

Glu Phe Arg Lys Gln Glu Val Leu Arg Lys Phe Arg Ala His Glu
            500             505             510

Thr Asn Leu Leu Ile Ala Thr Ser Ile Val Glu Glu Gly Val Asp Ile
            515             520             525

Pro Lys Cys Asn Leu Val Val Arg Phe Asp Leu Pro Thr Glu Tyr Arg
    530             535             540

Ser Tyr Val Gln Ser Lys Gly Arg Ala Arg Ala Pro Ile Ser Asn Tyr
545             550             555             560

Ile Met Leu Ala Asp Thr Asp Lys Ile Lys Ser Phe Glu Glu Asp Leu
                565             570             575

Lys Thr Tyr Lys Ala Ile Glu Lys Ile Leu Arg Asn Lys Cys Ser Lys
            580             585             590

Ser Val Asp Thr Gly Glu Thr Asp Ile Asp Pro Val Met Asp Asp Asp
            595             600             605

Asp Val Phe Pro Pro Tyr Val Leu Arg Pro Asp Asp Gly Gly Pro Arg
    610             615             620

Val Thr Ile Asn Thr Ala Ile Gly His Ile Asn Arg Tyr Cys Ala Arg
625             630             635             640

Leu Pro Ser Asp Pro Phe Thr His Leu Ala Pro Lys Cys Arg Thr Arg
                645             650             655

Glu Leu Pro Asp Gly Thr Phe Tyr Ser Thr Leu Tyr Leu Pro Ile Asn
            660             665             670

Ser Pro Leu Arg Ala Ser Ile Val Gly Pro Pro Met Ser Cys Val Arg
            675             680             685

Leu Ala Glu Arg Val Val Ala Leu Ile Cys Cys Glu Lys Leu His Lys
    690             695             700

Ile Gly Glu Leu Asp Asp His Leu Met Pro Val Gly Lys Glu Thr Val
705             710             715             720

Lys Tyr Glu Glu Glu Leu Asp Leu His Asp Glu Glu Thr Ser Val
                725             730             735

Pro Gly Arg Pro Gly Ser Thr Lys Arg Arg Gln Cys Tyr Pro Lys Ala
            740             745             750

Ile Pro Glu Cys Leu Arg Asp Ser Tyr Pro Arg Pro Asp Gln Pro Cys
            755             760             765

Tyr Leu Tyr Val Ile Gly Met Val Leu Thr Thr Pro Leu Pro Asp Glu
    770             775             780

Leu Asn Phe Arg Arg Arg Lys Leu Tyr Pro Pro Glu Asp Thr Thr Arg
785             790             795             800

Cys Phe Gly Ile Leu Thr Ala Lys Pro Ile Pro Gln Ile Pro His Phe
                805             810             815

Pro Val Tyr Thr Arg Ser Gly Glu Val Thr Ile Ser Ile Glu Leu Lys
            820             825             830
```

-continued

Lys Ser Gly Phe Met Leu Ser Leu Gln Met Leu Glu Leu Ile Thr Arg
          835                 840                 845

Leu His Gln Tyr Ile Phe Ser His Ile Leu Arg Leu Glu Lys Pro Ala
          850                 855                 860

Leu Glu Phe Lys Pro Thr Asp Ala Asp Ser Ala Tyr Cys Val Leu Pro
865                 870                 875                 880

Leu Asn Val Val Asn Asp Ser Ser Thr Leu Asp Ile Asp Phe Lys Phe
                    885                 890                 895

Met Glu Asp Ile Glu Lys Ser Glu Ala Arg Ile Gly Ile Pro Ser Thr
                900                 905                 910

Lys Tyr Thr Lys Glu Thr Pro Phe Val Phe Lys Leu Glu Asp Tyr Gln
          915                 920                 925

Asp Ala Val Ile Ile Pro Arg Tyr Arg Asn Phe Asp Gln Pro His Arg
          930                 935                 940

Phe Tyr Val Ala Asp Val Tyr Thr Asp Leu Thr Pro Leu Ser Lys Phe
945                 950                 955                 960

Pro Ser Pro Glu Tyr Glu Thr Phe Ala Glu Tyr Tyr Lys Thr Lys Tyr
                    965                 970                 975

Asn Leu Asp Leu Thr Asn Leu Asn Gln Pro Leu Leu Asp Val Asp His
                980                 985                 990

Thr Ser Ser Arg Leu Asn Leu Leu Thr Pro Arg His Leu Asn Gln Lys
          995                 1000                 1005

Gly Lys Ala Leu Pro Leu Ser Ser Ala Glu Lys Arg Lys Ala Lys
     1010                 1015                 1020

Trp Glu Ser Leu Gln Asn Lys Gln Ile Leu Val Pro Glu Leu Cys
     1025                 1030                 1035

Ala Ile His Pro Ile Pro Ala Ser Leu Trp Arg Lys Ala Val Cys
     1040                 1045                 1050

Leu Pro Ser Ile Leu Tyr Arg Leu His Cys Leu Leu Thr Ala Glu
     1055                 1060                 1065

Glu Leu Arg Ala Gln Thr Ala Ser Asp Ala Gly Val Gly Val Arg
     1070                 1075                 1080

Ser Leu Pro Ala Asp Phe Arg Tyr Pro Asn Leu Asp Phe Gly Trp
     1085                 1090                 1095

Lys Lys Ser Ile Asp Ser Lys Ser Phe Ile Ser Ile Ser Asn Ser
     1100                 1105                 1110

Ser Ser Ala Glu Asn Asp Asn Tyr Cys Lys His Ser Thr Ile Val
     1115                 1120                 1125

Pro Glu Asn Ala Ala His Gln Gly Ala Asn Arg Thr Ser Ser Leu
     1130                 1135                 1140

Glu Asn His Asp Gln Met Ser Val Asn Cys Arg Thr Leu Leu Ser
     1145                 1150                 1155

Glu Ser Pro Gly Lys Leu His Val Glu Val Ser Ala Asp Leu Thr
     1160                 1165                 1170

Ala Ile Asn Gly Leu Ser Tyr Asn Gln Asn Leu Ala Asn Gly Ser
     1175                 1180                 1185

Tyr Asp Leu Ala Asn Arg Asp Phe Cys Gln Gly Asn Gln Leu Asn
     1190                 1195                 1200

Tyr Tyr Lys Gln Glu Ile Pro Val Gln Pro Thr Thr Ser Tyr Ser
     1205                 1210                 1215

Ile Gln Asn Leu Tyr Ser Tyr Glu Asn Gln Pro Gln Pro Ser Asp
     1220                 1225                 1230

Glu Cys Thr Leu Leu Ser Asn Lys Tyr Leu Asp Gly Asn Ala Asn

```
                    1235                1240                1245

Lys Ser Thr Ser Asp Gly Ser Pro Val Met Ala Val Met Pro Gly
            1250                1255                1260

Thr Thr Asp Thr Ile Gln Val Leu Lys Gly Arg Met Asp Ser Glu
            1265                1270                1275

Gln Ser Pro Ser Ile Gly Tyr Ser Ser Arg Thr Leu Gly Pro Asn
            1280                1285                1290

Pro Gly Leu Ile Leu Gln Ala Leu Thr Leu Ser Asn Ala Ser Asp
            1295                1300                1305

Gly Phe Asn Leu Glu Arg Leu Glu Met Leu Gly Asp Ser Phe Leu
            1310                1315                1320

Lys His Ala Ile Thr Thr Tyr Leu Phe Cys Thr Tyr Pro Asp Ala
            1325                1330                1335

His Glu Gly Arg Leu Ser Tyr Met Arg Ser Lys Lys Val Ser Asn
            1340                1345                1350

Cys Asn Leu Tyr Arg Leu Gly Lys Lys Lys Gly Leu Pro Ser Arg
            1355                1360                1365

Met Val Val Ser Ile Phe Asp Pro Pro Val Asn Trp Leu Pro Pro
            1370                1375                1380

Gly Tyr Val Val Asn Gln Asp Lys Ser Asn Thr Asp Lys Trp Glu
            1385                1390                1395

Lys Asp Glu Met Thr Lys Asp Cys Met Leu Ala Asn Gly Lys Leu
            1400                1405                1410

Asp Glu Asp Tyr Glu Glu Glu Asp Glu Glu Glu Ser Leu Met
            1415                1420                1425

Trp Arg Ala Pro Lys Glu Glu Ala Asp Tyr Glu Asp Asp Phe Leu
            1430                1435                1440

Glu Tyr Asp Gln Glu His Ile Arg Phe Ile Asp Asn Met Leu Met
            1445                1450                1455

Gly Ser Gly Ala Phe Val Lys Lys Ile Ser Leu Ser Pro Phe Ser
            1460                1465                1470

Thr Thr Asp Ser Ala Tyr Glu Trp Lys Met Pro Lys Lys Ser Ser
            1475                1480                1485

Leu Gly Ser Met Pro Phe Ser Ser Asp Phe Glu Asp Phe Asp Tyr
            1490                1495                1500

Ser Ser Trp Asp Ala Met Cys Tyr Leu Asp Pro Ser Lys Ala Val
            1505                1510                1515

Glu Glu Asp Asp Phe Val Val Gly Phe Trp Asn Pro Ser Glu Glu
            1520                1525                1530

Asn Cys Gly Val Asp Thr Gly Lys Gln Ser Ile Ser Tyr Asp Leu
            1535                1540                1545

His Thr Glu Gln Cys Ile Ala Asp Lys Ser Ile Ala Asp Cys Val
            1550                1555                1560

Glu Ala Leu Leu Gly Cys Tyr Leu Thr Ser Cys Gly Glu Arg Ala
            1565                1570                1575

Ala Gln Leu Phe Leu Cys Ser Leu Gly Leu Lys Val Leu Pro Val
            1580                1585                1590

Ile Lys Arg Thr Asp Arg Glu Lys Ala Leu Cys Pro Thr Arg Glu
            1595                1600                1605

Asn Phe Asn Ser Gln Gln Lys Asn Leu Ser Val Ser Cys Ala Ala
            1610                1615                1620

Ala Ser Val Ala Ser Ser Arg Ser Ser Val Leu Lys Asp Ser Glu
            1625                1630                1635
```

```
Tyr Gly Cys Leu Lys Ile Pro Pro Arg Cys Met Phe Asp His Pro
1640                1645                1650

Asp Ala Asp Lys Thr Leu Asn His Leu Ile Ser Gly Phe Glu Asn
    1655                1660                1665

Phe Glu Lys Lys Ile Asn Tyr Arg Phe Lys Asn Lys Ala Tyr Leu
1670                1675                1680

Leu Gln Ala Phe Thr His Ala Ser Tyr His Tyr Asn Thr Ile Thr
    1685                1690                1695

Asp Cys Tyr Gln Arg Leu Glu Phe Leu Gly Asp Ala Ile Leu Asp
1700                1705                1710

Tyr Leu Ile Thr Lys His Leu Tyr Glu Asp Pro Arg Gln His Ser
    1715                1720                1725

Pro Gly Val Leu Thr Asp Leu Arg Ser Ala Leu Val Asn Asn Thr
1730                1735                1740

Ile Phe Ala Ser Leu Ala Val Lys Tyr Asp Tyr His Lys Tyr Phe
    1745                1750                1755

Lys Ala Val Ser Pro Glu Leu Phe His Val Ile Asp Asp Phe Val
1760                1765                1770

Gln Phe Gln Leu Glu Lys Asn Glu Met Gln Gly Met Asp Ser Glu
    1775                1780                1785

Leu Arg Arg Ser Glu Glu Asp Glu Glu Lys Glu Glu Asp Ile Glu
1790                1795                1800

Val Pro Lys Ala Met Gly Asp Ile Phe Glu Ser Leu Ala Gly Ala
    1805                1810                1815

Ile Tyr Met Asp Ser Gly Met Ser Leu Glu Thr Val Trp Gln Val
1820                1825                1830

Tyr Tyr Pro Met Met Arg Pro Leu Ile Glu Lys Phe Ser Ala Asn
    1835                1840                1845

Val Pro Arg Ser Pro Val Arg Glu Leu Leu Glu Met Glu Pro Glu
1850                1855                1860

Thr Ala Lys Phe Ser Pro Ala Glu Arg Thr Tyr Asp Gly Lys Val
    1865                1870                1875

Arg Val Thr Val Glu Val Val Gly Lys Gly Lys Phe Lys Gly Val
1880                1885                1890

Gly Arg Ser Tyr Arg Ile Ala Lys Ser Ala Ala Ala Arg Arg Ala
    1895                1900                1905

Leu Arg Ser Leu Lys Ala Asn Gln Pro Gln Val Pro Asn Ser
1910                1915                1920

<210> SEQ ID NO 2
<211> LENGTH: 859
<212> TYPE: PRT
<213> ORGANISM: Homo sapiens

<400> SEQUENCE: 2

Met Tyr Ser Gly Ala Gly Pro Ala Leu Ala Pro Pro Ala Pro Pro
1               5                   10                  15

Pro Ile Gln Gly Tyr Ala Phe Lys Pro Pro Pro Arg Pro Asp Phe Gly
            20                  25                  30

Thr Ser Gly Arg Thr Ile Lys Leu Gln Ala Asn Phe Phe Glu Met Asp
                35                  40                  45

Ile Pro Lys Ile Asp Ile Tyr His Tyr Glu Leu Asp Ile Lys Pro Glu
        50                  55                  60

Lys Cys Pro Arg Arg Val Asn Arg Glu Ile Val Glu His Met Val Gln
```

```
                65                  70                  75                  80
His Phe Lys Thr Gln Ile Phe Gly Asp Arg Lys Pro Val Phe Asp Gly
                    85                  90                  95

Arg Lys Asn Leu Tyr Thr Ala Met Pro Leu Pro Ile Gly Arg Asp Lys
                100                 105                 110

Val Glu Leu Glu Val Thr Leu Pro Gly Glu Gly Lys Asp Arg Ile Phe
                115                 120                 125

Lys Val Ser Ile Lys Trp Val Ser Cys Val Ser Leu Gln Ala Leu His
                130                 135                 140

Asp Ala Leu Ser Gly Arg Leu Pro Ser Val Pro Phe Glu Thr Ile Gln
145                 150                 155                 160

Ala Leu Asp Val Val Met Arg His Leu Pro Ser Met Arg Tyr Thr Pro
                    165                 170                 175

Val Gly Arg Ser Phe Phe Thr Ala Ser Glu Gly Cys Ser Asn Pro Leu
                180                 185                 190

Gly Gly Gly Arg Glu Val Trp Phe Gly Phe His Gln Ser Val Arg Pro
                195                 200                 205

Ser Leu Trp Lys Met Met Leu Asn Ile Asp Val Ser Ala Thr Ala Phe
210                 215                 220

Tyr Lys Ala Gln Pro Val Ile Glu Phe Val Cys Glu Val Leu Asp Phe
225                 230                 235                 240

Lys Ser Ile Glu Glu Gln Gln Lys Pro Leu Thr Asp Ser Gln Arg Val
                245                 250                 255

Lys Phe Thr Lys Glu Ile Lys Gly Leu Lys Val Glu Ile Thr His Cys
                260                 265                 270

Gly Gln Met Lys Arg Lys Tyr Arg Val Cys Asn Val Thr Arg Arg Pro
                275                 280                 285

Ala Ser His Gln Thr Phe Pro Leu Gln Gln Glu Ser Gly Gln Thr Val
                290                 295                 300

Glu Cys Thr Val Ala Gln Tyr Phe Lys Asp Arg His Lys Leu Val Leu
305                 310                 315                 320

Arg Tyr Pro His Leu Pro Cys Leu Gln Val Gly Gln Glu Gln Lys His
                325                 330                 335

Thr Tyr Leu Pro Leu Glu Val Cys Asn Ile Val Ala Gly Gln Arg Cys
                340                 345                 350

Ile Lys Lys Leu Thr Asp Asn Gln Thr Ser Thr Met Ile Arg Ala Thr
                355                 360                 365

Ala Arg Ser Ala Pro Asp Arg Gln Glu Glu Ile Ser Lys Leu Met Arg
                370                 375                 380

Ser Ala Ser Phe Asn Thr Asp Pro Tyr Val Arg Glu Phe Gly Ile Met
385                 390                 395                 400

Val Lys Asp Glu Met Thr Asp Val Thr Gly Arg Val Leu Gln Pro Pro
                405                 410                 415

Ser Ile Leu Tyr Gly Gly Arg Asn Lys Ala Ile Ala Thr Pro Val Gln
                420                 425                 430

Gly Val Trp Asp Met Arg Asn Lys Gln Phe His Thr Gly Ile Glu Ile
                435                 440                 445

Lys Val Trp Ala Ile Ala Cys Phe Ala Pro Gln Arg Gln Cys Thr Glu
                450                 455                 460

Val His Leu Lys Ser Phe Thr Glu Gln Leu Arg Lys Ile Ser Arg Asp
465                 470                 475                 480

Ala Gly Met Pro Ile Gln Gly Gln Pro Cys Phe Cys Lys Tyr Ala Gln
                485                 490                 495
```

Gly Ala Asp Ser Val Glu Pro Met Phe Arg His Leu Lys Asn Thr Tyr
                500                 505                 510

Ala Gly Leu Gln Leu Val Val Ile Leu Pro Gly Lys Thr Pro Val
            515                 520                 525

Tyr Ala Glu Val Lys Arg Val Gly Asp Thr Val Leu Gly Met Ala Thr
        530                 535                 540

Gln Cys Val Gln Met Lys Asn Val Gln Arg Thr Thr Pro Gln Thr Leu
545                 550                 555                 560

Ser Asn Leu Cys Leu Lys Ile Asn Val Lys Leu Gly Gly Val Asn Asn
                565                 570                 575

Ile Leu Leu Pro Gln Gly Arg Pro Pro Val Phe Gln Gln Pro Val Ile
                580                 585                 590

Phe Leu Gly Ala Asp Val Thr His Pro Pro Ala Gly Asp Gly Lys Lys
                595                 600                 605

Pro Ser Ile Ala Ala Val Val Gly Ser Met Asp Ala His Pro Asn Arg
                610                 615                 620

Tyr Cys Ala Thr Val Arg Val Gln Gln His Arg Gln Glu Ile Ile Gln
625                 630                 635                 640

Asp Leu Ala Ala Met Val Arg Glu Leu Leu Ile Gln Phe Tyr Lys Ser
                645                 650                 655

Thr Arg Phe Lys Pro Thr Arg Ile Ile Phe Tyr Arg Asp Gly Val Ser
                660                 665                 670

Glu Gly Gln Phe Gln Gln Val Leu His His Glu Leu Leu Ala Ile Arg
                675                 680                 685

Glu Ala Cys Ile Lys Leu Glu Lys Asp Tyr Gln Pro Gly Ile Thr Phe
                690                 695                 700

Ile Val Val Gln Lys Arg His His Thr Arg Leu Phe Cys Thr Asp Lys
705                 710                 715                 720

Asn Glu Arg Val Gly Lys Ser Gly Asn Ile Pro Ala Gly Thr Thr Val
                725                 730                 735

Asp Thr Lys Ile Thr His Pro Thr Glu Phe Asp Phe Tyr Leu Cys Ser
                740                 745                 750

His Ala Gly Ile Gln Gly Thr Ser Arg Pro Ser His Tyr His Val Leu
                755                 760                 765

Trp Asp Asp Asn Arg Phe Ser Ser Asp Glu Leu Gln Ile Leu Thr Tyr
770                 775                 780

Gln Leu Cys His Thr Tyr Val Arg Cys Thr Arg Ser Val Ser Ile Pro
785                 790                 795                 800

Ala Pro Ala Tyr Tyr Ala His Leu Val Ala Phe Arg Ala Arg Tyr His
                805                 810                 815

Leu Val Asp Lys Glu His Asp Ser Ala Glu Gly Ser His Thr Ser Gly
                820                 825                 830

Gln Ser Asn Gly Arg Asp His Gln Ala Leu Ala Lys Ala Val Gln Val
                835                 840                 845

His Gln Asp Thr Leu Arg Thr Met Tyr Phe Ala
    850                 855

<210> SEQ ID NO 3
<211> LENGTH: 77
<212> TYPE: RNA
<213> ORGANISM: Artificial Sequence
<220> FEATURE:
<223> OTHER INFORMATION: Synthetic- AR CAG hairpin (AR-3-21)

<400> SEQUENCE: 3

```
ugcugcugcu gcagcagcag cagcagcagc agcagcagca gcagcagcag cagcagcagc    60
agcagcagca gcagcaa                                                   77
```

<210> SEQ ID NO 4
<211> LENGTH: 53
<212> TYPE: DNA
<213> ORGANISM: Artificial Sequence
<220> FEATURE:
<223> OTHER INFORMATION: Synthetic- pTIP-shCAG/CUG

<400> SEQUENCE: 4

```
gcagcagcag cagcagcagc agctcgagcu gcugcugcug cugcugcugt ttt           53
```